United States Patent
Yachie et al.

(10) Patent No.: US 11,584,951 B2
(45) Date of Patent: Feb. 21, 2023

(54) METHOD FOR INTEGRALLY DETECTING NONDESTRUCTIVE MEASUREMENT INFORMATION AND GENOME-RELATED INFORMATION OF ONE CELL

(71) Applicant: The University of Tokyo, Tokyo (JP)

(72) Inventors: Nozomu Yachie, Tokyo (JP); Sadao Ota, Tokyo (JP)

(73) Assignee: The University of Tokyo, Tokyo (JP)

( * ) Notice: Subject to any disclaimer, the term of this patent is extended or adjusted under 35 U.S.C. 154(b) by 157 days.

(21) Appl. No.: 16/610,232

(22) PCT Filed: May 2, 2018

(86) PCT No.: PCT/JP2018/017567
§ 371 (c)(1),
(2) Date: Jan. 13, 2020

(87) PCT Pub. No.: WO2018/203576
PCT Pub. Date: Nov. 8, 2018

(65) Prior Publication Data
US 2020/0131562 A1    Apr. 30, 2020

(30) Foreign Application Priority Data

May 2, 2017    (JP) .............................. JP2017-091961

(51) Int. Cl.
C12Q 1/6806 (2018.01)
C12Q 1/686 (2018.01)
G01N 21/64 (2006.01)

(52) U.S. Cl.
CPC ........... *C12Q 1/6806* (2013.01); *C12Q 1/686* (2013.01); *G01N 21/6428* (2013.01); *G01N 2021/6439* (2013.01)

(58) Field of Classification Search
CPC ................ C12Q 1/6869; C12Q 1/6834; C12Q 2543/10; C12Q 2563/149; C12Q 2563/159; C12Q 2565/519; C12Q 2565/601; C12Q 2565/629; C12Q 1/6806; C12Q 1/686; C12Q 2563/179; G01N 21/6428; G01N 2021/6439
See application file for complete search history.

(56) References Cited

U.S. PATENT DOCUMENTS

| | | | |
|---|---|---|---|
| 9,260,753 B2 * | 2/2016 | Xie | C12N 15/1065 |
| 2009/0042737 A1 | 2/2009 | Katz et al. | |
| 2012/0220494 A1 * | 8/2012 | Samuels | C12N 15/1075 |
| | | | 506/26 |
| 2018/0088112 A1 * | 3/2018 | Fan | G01N 33/566 |

FOREIGN PATENT DOCUMENTS

| | | | | |
|---|---|---|---|---|
| JP | 2010-535511 A | 11/2010 | | |
| JP | 2013-508156 A | 3/2013 | | |
| WO | WO-2015/031691 A1 | 3/2015 | | |
| WO | WO 2015/164212 A1 | 10/2015 | | |
| WO | WO 2015/166768 A1 | 11/2015 | | |
| WO | WO-2016191533 A1 * | 12/2016 | .......... | C12Q 1/6834 |
| WO | WO-2017/053905 A1 | 3/2017 | | |
| WO | WO-2018/058073 A2 | 3/2018 | | |

OTHER PUBLICATIONS

Office Action on Japanese Application No. 2019-515752 related to U.S. Appl. No. 16/610,232 dated Oct. 30, 2020 (5 pages).
International Search Report dated Jul. 31, 2018, in PCT/JP2018/017567.
Garstecki et al., "Formation of monodisperse bubbles in a microfluidic flow-focusing device," Appl. Phys. Lett., Sep. 27, 2004, 85:2649-2561.
Gierahn et al., "Seq-Well: portable, low-cost RNA sequencing of single cells at high throughput," Nature Methods, Apr. 2017, 14(4):395-398, with Erratum.
Klein et al., "Droplet barcoding for single cell transcriptomics applied to embryonic stem cells," Cell, May 21, 2015, 161(5):1187-1201.
Macosko et al., "Highly Parallel Genome-wide Expression Profiling of Individual Cells Using Nanoliter Droplets," Cell, May 21, 2015, 161(5):1202-1214.
Nie et al., "Emulsification of a microfluidic flow-focusing device: Effect of the viscosities of the liquids," Microfluidics and Nanofluidics, Jan. 2008, 5:585-594.
Sambrook et al., Eds., Molecular Cloning, a Laboratory Manual, 3$^{rd}$ Ed., 2001, vol. 1, 7.13-7.17 and 7.42-7.50.
Supplementary European Search Report dated Dec. 14, 2020 in EP 18794986.2.

* cited by examiner

*Primary Examiner* — David C Thomas
(74) *Attorney, Agent, or Firm* — Foley & Lardner LLP

(57) ABSTRACT

The present invention provides a method for integrally detecting nondestructive measurement information and genome-related information of single cells.
More specifically, the present invention uses a method including:
  preparing a plurality of compartments containing single cell or a derivative thereof, a first bead(s), and a second bead(s) per compartment;
  detecting both nondestructive measurement information of single cell and imaging information of the first bead(s) and associating the nondestructive measurement information of single cell with the imaging information of the first bead(s) before preparation of each compartment or in each compartment;
  obtaining a hybridized complex;
  producing an amplified product derived from the hybridized complex; and
  integrally detecting nondestructive measurement information and genome-related information in single cell.

21 Claims, 21 Drawing Sheets

[FIG. 1b]
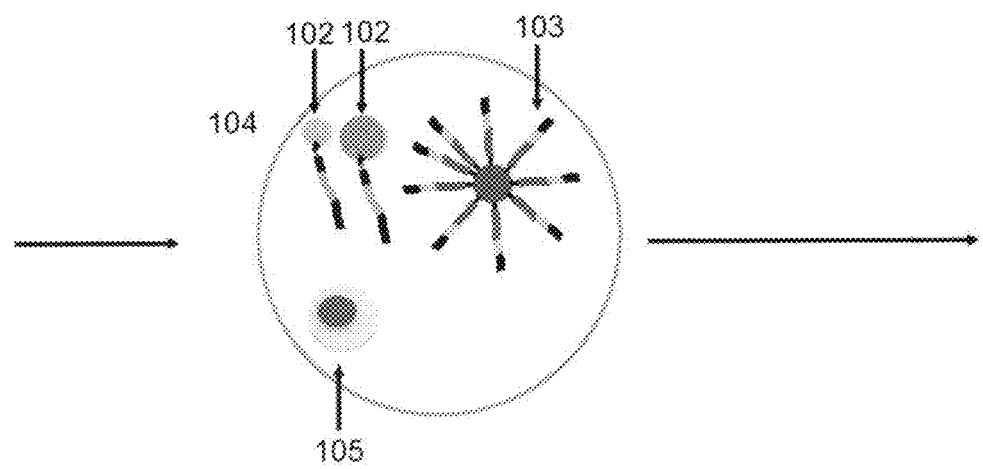

[FIG. 2]
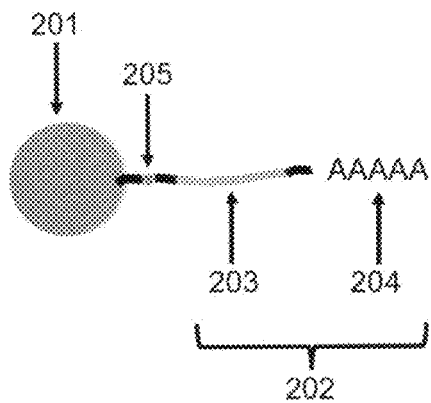
[FIG. 3]
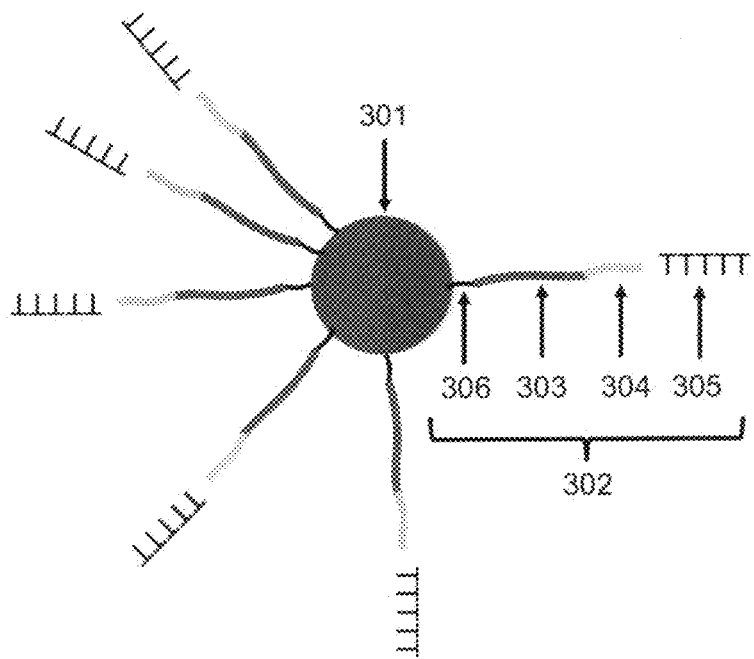

[FIG. 12]
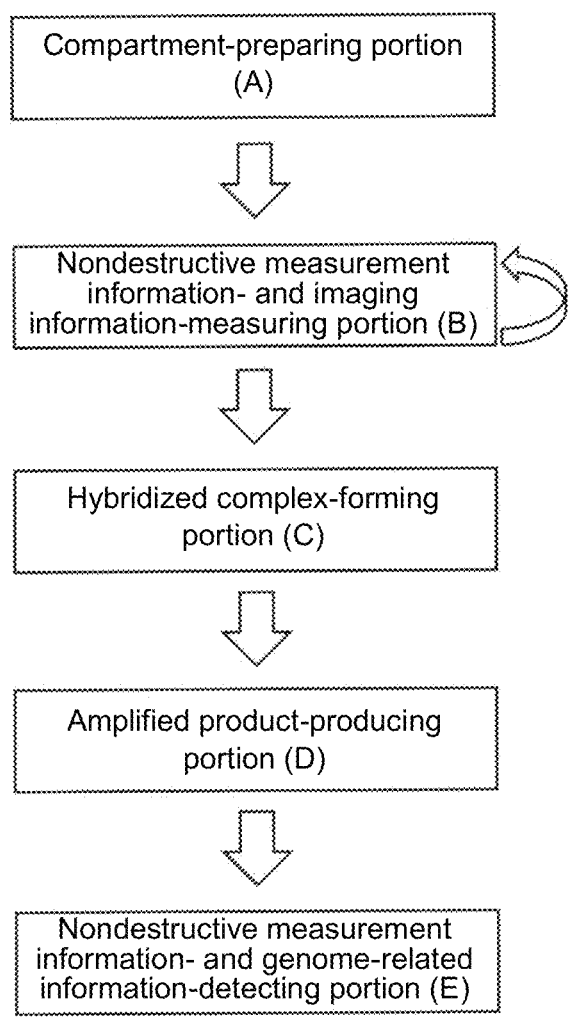

[FIG. 13]
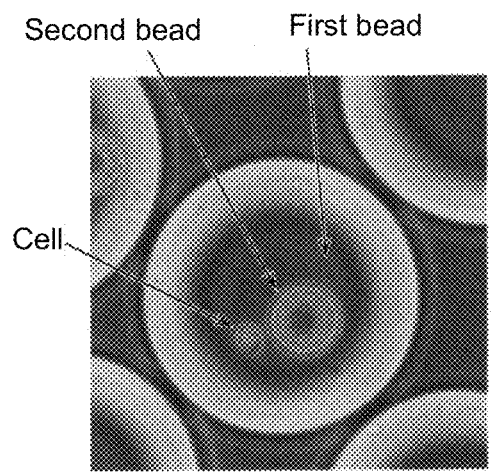
[FIG. 14]
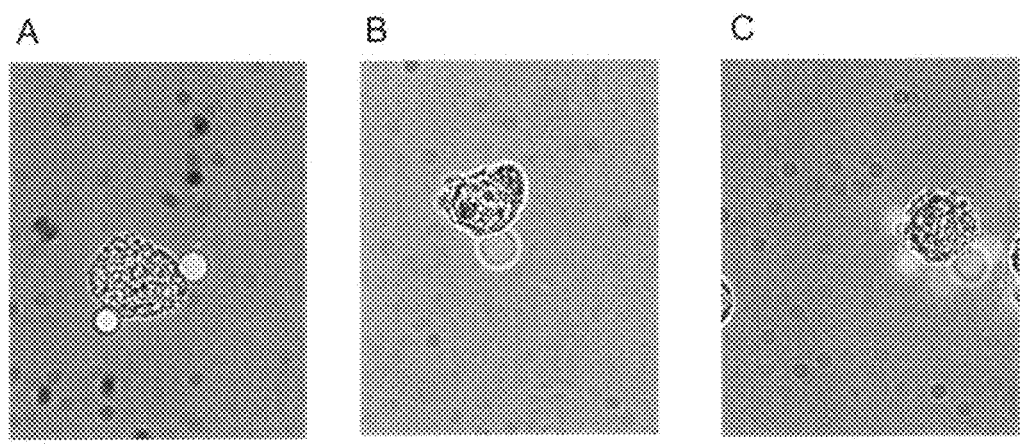

[FIG. 15]
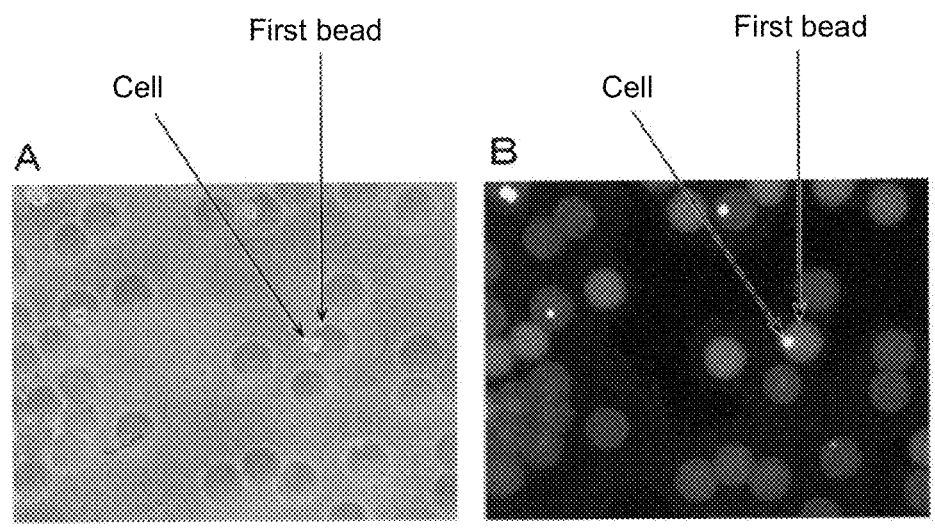
[FIG. 16]
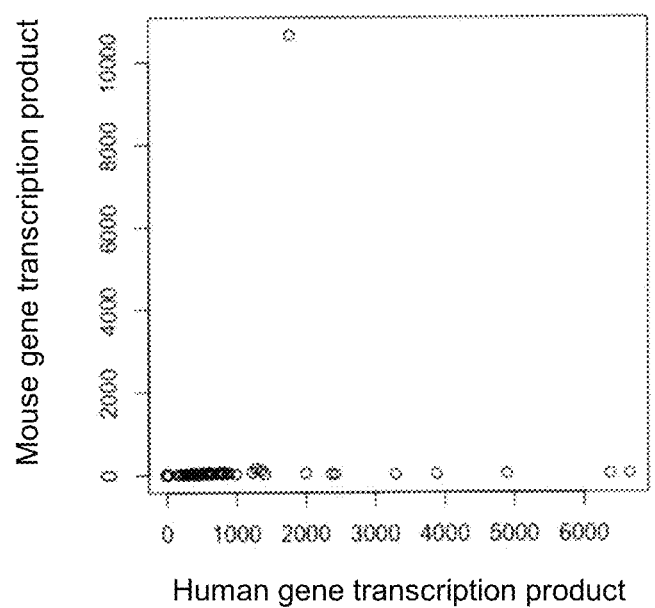

[FIG. 17]
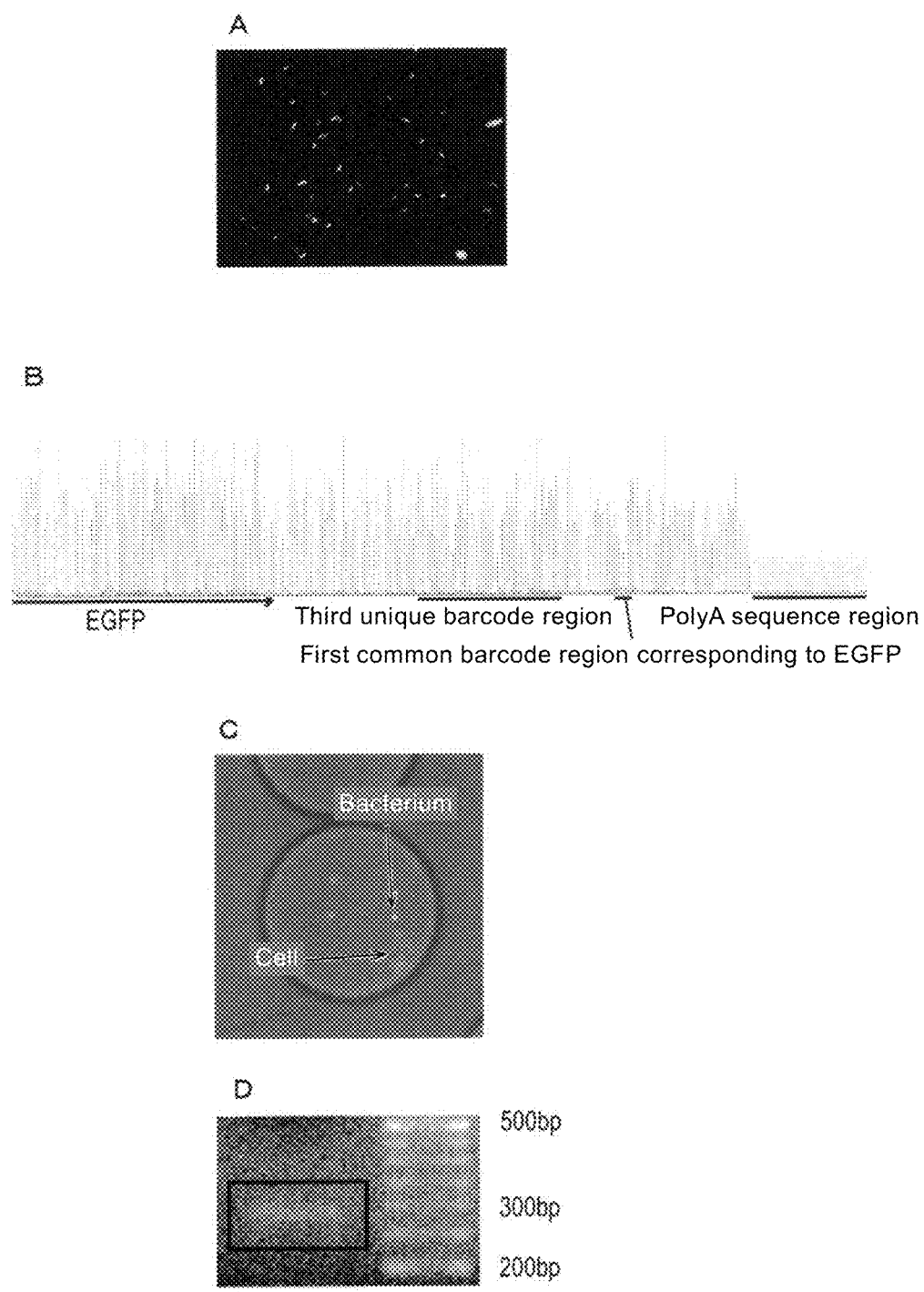

METHOD FOR INTEGRALLY DETECTING NONDESTRUCTIVE MEASUREMENT INFORMATION AND GENOME-RELATED INFORMATION OF ONE CELL

CROSS-REFERENCE TO RELATED APPLICATIONS

This application is the U.S. National Stage of PCT/JP2018/017567, filed May 2, 2018, which is based upon and claims the benefit of priority from Japanese Patent Application No. 2017-091961, filed on May 2, 2017; the entire contents of which are incorporated herein by reference.

BACKGROUND OF THE INVENTION

Field of the Invention

The present invention relates to a method for integrally detecting nondestructive measurement information and genome-related information of single cells.

Background Art

A cell is a minimum unit constituting an organism. Heretofore, elucidation of the functions, structures, forms and the like of organisms had been attempted only for cell populations. However, recent studies have revealed that gene expression varies and is diverse depending on cells even in similar cell types such as cancer tissues, and there is a need for elucidating gene expression, etc., of individual cells.

For this purpose, at present, as a method for detecting transcription products derived from one cell, a method for obtaining data on genetic information of cells using beads to which oligonucleotides containing barcode sequences are bound and using sequencing techniques is known. (Patent Literature 1, Non Patent Literature 1)

Meanwhile, it has been known that imaging techniques including microscopy are used to identify the morphological information of cells. Use of imaging techniques such as microscopy or imaging cytometry enables obtaining nondestructive measurement information of individual cells.

However, data on cells measured by the above imaging techniques and sequencing techniques can be associated only by selective and physical cell sorting. For example, in order to obtain the information of the genome of imaged cells, processes of physically capturing a single cell, compartmentalizing, lysing the cell, and amplifying nucleic acids should be independently performed for individual cells. Such a method is low throughput and high cost. Thus, it was difficult to associate nondestructive measurement information with genetic information of a single cell.

Furthermore, at present, cytomorphological information taken by imaging techniques is visually evaluated. Even when discrimination will be advanced by machine learning technology, the validity of the discrimination should be evaluated. Under present circumstances, for visually observed a single cell, there is no other choice but to physically sort and compare with genetic and other diagnostic techniques.

Under such a technical situation, it can be said that there is a need for a means of integrally detecting nondestructive measurement information and genome-related information of single cells in order to enhance the mutual use of nondestructive measurement information and genome-related information of single cells and the value between respective pieces of information.

CITATION LIST

Non Patent Literature

Non Patent Literature 1
E. Z. Macosko et al., Highly Parallel Genome-wide Expression Profiling of Individual Cells Using Nanoliter Droplets. Cell. 161, 1202-1214 (2015)

Patent Literature

Patent Literature 1
WO 2015/166768 A

SUMMARY OF THE INVENTION

An object of the present invention is to integrally detect nondestructive measurement information and genome-related information of single cells.

Now, the present inventors have found that when, together with a single cell or a derivative thereof, a plurality of beads linked to a barcode nucleic acid are contained in one compartment, and nondestructive measurement information of the single cell is associated with imaging information of the beads, and then genome-related information is measured and associated, nondestructive measurement information and genome-related information of the single cell can be integrally and effectively detected. Association of nondestructive measurement information of the single cell with imaging information of the bead may be performed between the single cell and the bead before contained in the compartment. The present invention is based on the finding.

The present invention encompasses the following inventions:

(1) A method for integrally detecting nondestructive measurement information and genome-related information of single cells, the method including:

preparing a plurality of compartments containing a single cell or a derivative thereof, a first bead(s), and a second bead(s) per compartment, wherein each first bead is a particle cleavably linked to a first barcode nucleic acid corresponding to each imaging information or an organism containing a first barcode nucleic acid corresponding to each imaging information, and imaging information of the first bead(s) in each compartment can be clearly distinguished from each other, and the second bead(s) is linked to a plurality of second barcode nucleic acids hybridizable with a genome-related nucleic acid corresponding to a cell genome or an expressed product thereof or the first barcode nucleic acid;

detecting both nondestructive measurement information of the single cell and imaging information of the first bead(s) and associating the nondestructive measurement information of the single cell with the imaging information of the first bead(s) before preparation of each compartment or in each compartment;

cleaving the first barcode nucleic acid from the associated first bead(s), and hybridizing each of the genome-related nucleic acid and the first barcode nucleic acid with the second barcode nucleic acid to obtain a hybridized complex;

producing an amplified product derived from the hybridized complex; and integrally detecting nondestructive measurement information and genome-related information in the single cell using an expression pattern of the amplified product as an index.

(2) The method according to (1), wherein the plurality of compartments are obtained by partitioning a cell group or a derivative thereof, a plurality of first beads, and a plurality of second beads.

(3) The method according to (1) or (2), wherein
nondestructive measurement information of the single cell is detected using an expression pattern of a first amplified product derived from a hybridized complex of the first barcode nucleic acid with the second barcode nucleic acid as an index, and
genome-related information of the single cell is detected using an expression pattern of a second amplified product derived from a hybridized complex of the genome-related nucleic acid with the second barcode nucleic acid as an index.

(4) The method according to any one of (1) to (3), wherein the number of the first beads per compartment is plural.

(5) The method according to any one of (1) to (4), wherein the number of the second beads per compartment is one.

(6) The method according to any one of (1) to (5), wherein the compartment is in a form of a well, a droplet, or a gel particle.

(7) The method according to any one of (1) to (6), wherein the genome-related nucleic acid is a genome DNA of the single cell, an RNA derived from a genome of the single cell or a cDNA thereof, or a nucleic acid probe specific to a protein expressed in the single cell.

(8) The method according to any one of (1) to (7), wherein the nondestructive measurement information is based on at least one piece of measurement information selected from color, fluorescence, size, shape, electromagnetic wave, transmission, phase, scattering, reflection, coherent Raman, Raman, and absorption spectrum.

(9) The method according to any one of (1) to (8), wherein each first barcode nucleic acid in the first bead(s) contains a first common barcode region which is common in the first bead(s) corresponding to same imaging information and a first hybridize region hybridizable with the second barcode nucleic acid.

(10) The method according to any one of (1) to (9), wherein sequence information of the first common barcode region becomes an index for identifying nondestructive measurement information of the single cell.

(11) The method according to any one of (1) to (10), wherein each of the plurality of second barcode nucleic acids linked to the second bead(s) includes a second common barcode region which is in common with each other, a second unique barcode region which can be clearly distinguished from each other, and a second hybridize region hybridizable with the genome-related nucleic acid or the first barcode nucleic acid.

(12) The method according to (11), wherein sequence information of the second common barcode region becomes an index for identifying the single cell or a derivative thereof existing in the compartment.

(13) The method according to (11) or (12), wherein sequence information of the second unique barcode region becomes an index for identifying the genome-related nucleic acid.

(14) The method according to any one of (1) to (13), wherein the second barcode nucleic acid further includes a PCR primer region.

(15) The method according to (14), wherein the second barcode nucleic acid includes the PCR primer region, the second common barcode region, the second unique barcode region, and the second hybridize region in this order from the second bead side.

(16) The method according to any one of (11) to (15), wherein the second hybridize region includes the first hybridize region or a nucleic acid complementary to the genome-related nucleic acid.

(17) The method according to any one of (1) to (16), wherein the first barcode nucleic acid and the second barcode nucleic acid are a RNA, a DNA, or a combination thereof.

(18) The method according to any one of (1) to (17), wherein the nondestructive measurement information is measured by flow cytometry or microscopy.

(19) The method according to any one of (1) to (18), wherein the nondestructive measurement information is imaging information.

(20) The method according to any one of (1) to (18), wherein the nondestructive measurement information is morphological information of a cell.

(21) A system for integrally detecting nondestructive measurement information and genome-related information of single cells, the system including:
a compartment-preparing portion which prepares a plurality of compartments containing a single cell or a derivative thereof, a first bead(s), and a second bead(s) per compartment,
wherein each first bead is
a particle cleavably linked to a first barcode nucleic acid corresponding to each imaging information or
an organism containing a first barcode nucleic acid corresponding to each imaging information, and
imaging information of the first bead(s) in each compartment can be clearly distinguished from each other, and
the second bead(s) is linked to a plurality of second barcode nucleic acids hybridizable with a genome-related nucleic acid corresponding to a cell genome or an expressed product thereof or the first barcode nucleic acid;
a nondestructive measurement information-measuring portion which measures both nondestructive measurement information of the single cell and imaging information of the first bead(s) and associates the nondestructive measurement information of the single cell with the imaging information of the first bead(s) before preparation of each compartment or in each compartment;
a hybridized complex-forming portion which cleaves a first barcode nucleic acid corresponding to each imaging information from the associated first bead(s), and hybridizes each of the genome-related nucleic acid and the first barcode nucleic acid with the second barcode nucleic acid to obtain a hybridized complex;
an amplified product-producing portion which produces an amplified product derived from the hybridized complex; and
a nondestructive measurement information- and genome-related information-detecting portion which integrally detects nondestructive measurement information and genome-related information in the single cell using an expression pattern of the amplified product as an index.

(22) The system according to (21), wherein the nondestructive measurement information- and imaging information-measuring portion includes at least one selected from a microscope and a flow cytometer.

(23) A combination of a first bead(s) and a second bead(s) for integrally detecting nondestructive measurement information and genome-related information of single cells, wherein the first bead(s) is
  a particle(s) cleavably linked to a first barcode nucleic acid corresponding to each imaging information or
  an organism(s) containing a first barcode nucleic acid corresponding to each imaging information,
the second bead(s) is linked to a plurality of second barcode nucleic acids hybridizable with a genome-related nucleic acid corresponding to a cell genome or an expressed product thereof or the first barcode nucleic acid,
nondestructive measurement information of a single cell can be detected using an expression pattern of a first amplified product derived from a hybridized complex of the first barcode nucleic acid with the second barcode nucleic acid as an index, and genome-related information of the single cell can be detected using an expression pattern of a second amplified product derived from a hybridized complex of the genome-related nucleic acid with the second barcode nucleic acid as an index.

(24) A detecting agent including a first bead(s), which is used together with a second bead(s) for integrally detecting nondestructive measurement information and genome-related information of single cells, wherein
the first bead(s) is
  a particle(s) cleavably linked to a first barcode nucleic acid corresponding to each imaging information or
  an organism(s) containing a first barcode nucleic acid corresponding to each imaging information,
the second bead(s) is linked to a plurality of second barcode nucleic acids hybridizable with a genome-related nucleic acid corresponding to a cell genome or an expressed product thereof or the first barcode nucleic acid,
nondestructive measurement information of a single cell can be detected using an expression pattern of a first amplified product derived from a hybridized complex of the first barcode nucleic acid with the second barcode nucleic acid as an index, and genome-related information of the single cell can be detected using an expression pattern of a second amplified product derived from a hybridized complex of the genome-related nucleic acid with the second barcode nucleic acid as an index.

(25) A detecting agent including a second bead(s), which is used together with a first bead(s) for integrally detecting nondestructive measurement information and genome-related information of single cells, wherein
the first bead(s) is
  a particle(s) cleavably linked to a first barcode nucleic acid corresponding to each imaging information or
  an organism(s) containing a first barcode nucleic acid corresponding to each imaging information,
the second bead(s) is linked to a plurality of second barcode nucleic acids hybridizable with a genome-related nucleic acid corresponding to a cell genome or an expressed product thereof or the first barcode nucleic acid,
nondestructive measurement information of a single cell can be detected using an expression pattern of a first amplified product derived from a hybridized complex of the first barcode nucleic acid with the second barcode nucleic acid as an index, and genome-related information of a single cell can be detected using an expression pattern of a second amplified product derived from a hybridized complex of the genome-related nucleic acid with the second barcode nucleic acid as an index.

(26) A method for classifying a test cell, based on nondestructive measurement information in the test cell, using a classification model obtained based on the nondestructive measurement information and the genome-related information integrally detected by the method according to any one of (1) to (20).

(27) A method for obtaining nondestructive measurement information and genome-related information of single cells for a test substance, using the method for integrally detecting nondestructive measurement information and genome-related information of single cells according to any one of (1) to (20), the method including:
including making the test substance coexist with a single cell or a derivative thereof, the first bead(s), and the second bead(s).

(28) A method for screening a test substance, using the nondestructive measurement information and the genome-related information of the single cell for the test substance obtained by the method according to (27).

According to the present invention, nondestructive measurement information and genome-related information of one cell can be integrally and effectively detected.

BRIEF DESCRIPTION OF THE DRAWINGS

FIG. 2 is a schematic diagram on a first bead(s) cleavably linked to a first barcode nucleic acid of the present invention.

FIG. 3 is a schematic diagram on a second bead(s) linked to a second barcode nucleic acid of the present invention.

FIG. 12 is a flow chart of a system of the present invention.

FIG. 13 is a photograph of a water-in-oil compartment containing the first bead(s), the second bead(s), and an NIH3T3 cell.

FIG. 14A is a composite photograph of a green fluorescent bead-carrying NIH3T3 cell taken by a fluorescence microscope and a bright field microscope. FIG. 14B is a composite photograph of a red fluorescent bead-carrying K562 cell taken by a fluorescence microscope and a bright field microscope. FIG. 14C is a composite photograph of a green fluorescent bead- and red fluorescent bead-carrying MIA-PaCa2 cell taken by a fluorescence microscope and a bright field microscope.

FIG. 15A is a phase-contrast micrograph of the first bead(s) containing a cell. FIG. 15B is a composite photograph of the first bead(s) containing a cell taken by a fluorescence microscope and a bright field microscope.

FIG. 16 is a result of measurement of the number of gene transcription products in the compartment.

FIG. 17A is a composite photograph of a mixture of bacteria containing the first barcode nucleic acid taken by a fluorescence microscope and a bright field microscope. FIG. 17B is a result of sequencing of the sequence of a plasmid having an EGFP protein gene region and a first common barcode region. FIG. 17C is a photograph of a water-in-oil compartment containing a cell and a bacterium containing the first barcode nucleic acid. FIG. 17D is a photograph of electrophoresis of an amplified product containing the sequence of a third unique barcode region and a first common barcode region corresponding to EGFP.

DETAILED DESCRIPTION OF THE INVENTION

Definition

Figure 1A:
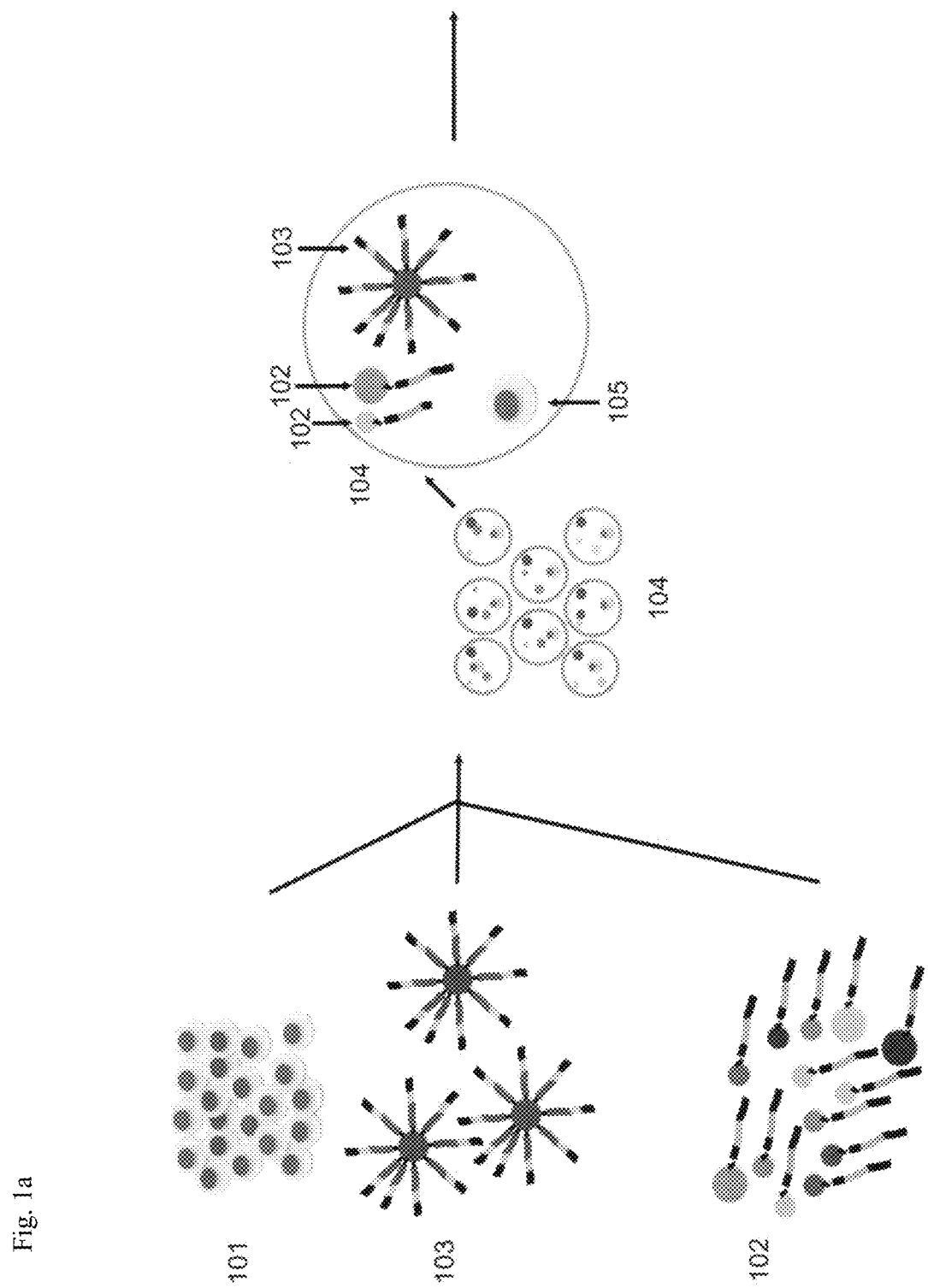
FIG. 1 is a schematic diagram on a detection method of the present invention.

"Genome-related information" as used herein means nucleic acid sequence information derived from a genome-related nucleic acid corresponding to a cell genome or an expressed product thereof. Here, "genome-related nucleic acid" means preferably a genome DNA of a single cell, an RNA such as an mRNA derived from a genome of a single cell or a cDNA thereof, or a nucleic acid probe specific to a molecule such as a protein expressed in a single cell. The nucleic acid probe preferably contains a barcode nucleic acid which is cleavably linked to a molecule specifically binding to a molecule such as a target protein (hereinafter also referred to as binding molecule) and which can be clearly distinguished from each other. When the nucleic acid is a genome DNA, the DNA may be a fragment cleaved by a restriction enzyme, etc., or a DNA tag may be introduced thereinto.

"Barcode region" as used herein is a region of a random base sequence consisting of T (thymine) or U (uracil), A (adenine), G (guanine), and C (cytosine). The barcode nucleic acid is a nucleic acid containing the barcode region and enables discrimination of genome-related information of a cell and imaging information derived from a bead.

As the barcode regions, two types of a common barcode region and a unique barcode region exist.

The common barcode region is a barcode region common in the same subject to be discriminated. When the subject to be discriminated is genome-related information of a cell, the common barcode region is a barcode region different for each cell, namely, a barcode region common in one cell. Labelling with the common barcode region enables discrimination of genome-related information derived from the same cell. When the subject to be discriminated is imaging information of a bead, the common barcode region is a barcode region different for each bead having the same imaging information, namely, a barcode region common in a bead having the same imaging information. Labeling with the common barcode region enables discrimination of imaging information derived from a bead having the same imaging information.

Furthermore, in the nucleic acid probe specific to a molecule such as a protein expressed in a single cell, the nucleic acid probe contains a molecule specifically binding to the molecule such as a protein (binding molecule). Here, in the nucleic acid probe, a barcode region different for each of the binding molecules, namely, a barcode region common in the same binding molecule is also regarded as the common barcode region.

The unique barcode region enables clear distinction of each barcode nucleic acid by labeling with a barcode region different for each barcode nucleic acid, and can discriminate a bead linked to each barcode nucleic acid and a genome-related nucleic acid hybridized with each barcode nucleic acid. The length of the barcode region is not particularly limited, and is preferably a sequence of 10 to 40 bases in length. For example, when the barcode region is 12 bases in length, $4^{12}$ types of diverse barcode sequences can be subjected to nucleic acid amplification once, and $4^{12}$ types of beads can be produced.

"Hybridize" as used herein means that a hybridize region of a barcode nucleic acid forms a double-stranded complex with a genome-related nucleic acid corresponding to a cell genome or an expressed product thereof or another barcode nucleic acid under a stringent condition. Here, the stringent condition means, as it is called, a condition in which a specific complex is formed and no non-specific complex is formed. Such a stringent condition is known to a person skilled in the art, and can be set with reference to, for example, Molecular Cloning (Third Edition, Cold Spring Harbor Laboratory Press, New York) or Current protocols in molecular biology (edited by Frederick M. Ausubel et al., 1987).

Therefore, "hybridize region" is a region which can bind to (can be hybridized with) a genome-related nucleic acid corresponding to a cell genome or an expressed product thereof or another barcode nucleic acid.

For example, when the genome-related nucleic acid is an mRNA, a second hybridize region in a second barcode nucleic acid is preferably polythymine composed of T. The length of polythymine may be a length at which polythymine can be annealed (can be hybridized) with a polyadenine (A) tail of the mRNA. In the above case, a first hybridize region is preferably a sequence complementary to polythymine, for example, polyadenine (polyA).

When the genome-related nucleic acid is a DNA such as a genome DNA, the second hybridize region in the second barcode nucleic acid preferably includes a sequence complementary to a particular sequence of the DNA or a sequence of a DNA tag introduced into the DNA. In the above case, the first hybridize region is preferably a sequence complementary to the second hybridize region.

When the nucleic acid probe specific to a molecule such as a protein expressed in a single cell contains a barcode nucleic acid, and the barcode nucleic acid contains a hybridize region, the second hybridize region in the second barcode nucleic acid preferably includes a sequence complementary to the hybridize region. In the above case, the above hybridize region in the barcode nucleic acid linked to the nucleic acid probe is preferably a sequence complementary to the second hybridize region.

"Compartment" as used herein is a space isolated from other liquids or surrounding vehicles. Preferably, the compartment is a certain volume of a liquid or a gel retained in the above space. The above compartment is also referred to as micro-compartment. Isolation between the compartment and the surrounding can be obtained from a solid barrier around the compartment or phase separation. For example, an aqueous droplet suspended in a hydrophobic carrier solution may constitutes the compartment. The above compartment may be in a form of a well, a droplet, and a gel particle, and specific examples thereof include an aqueous droplet, an oil droplet, a gel particle of a hydrogel (e.g., agarose, collagen, alginic acid), a water-oil structure in which a plurality of non-mixed interfaces overlap such as an emulsion, a well such as a multiwell plate and the like.

Detection Method

A method for integrally detecting nondestructive measurement information and genome-related information of single cells of the present invention is characterized by including:

preparing a plurality of compartments containing a single cell or a derivative thereof, a first bead(s), and a second bead(s) per compartment, wherein each first bead is a particle cleavably linked to a first barcode nucleic acid corresponding to each imaging information or an organism containing a first barcode nucleic acid corresponding to each imaging information, and imaging information of the first bead(s) in each compartment can be clearly distinguished from each other, and the second bead(s) is linked to a plurality of second barcode nucleic acids hybridizable with a genome-related nucleic acid corresponding to a cell genome or an expressed product thereof or the first barcode nucleic acid;

detecting both nondestructive measurement information of the single cell and imaging information of the first bead(s) and associating the nondestructive measurement information of the single cell with the imaging information of the first bead(s) before preparation of each compartment or in each compartment;

cleaving the first barcode nucleic acid from the associated first bead(s), and hybridizing each of the genome-related nucleic acid and the first barcode nucleic acid with the second barcode nucleic acid to obtain a hybridized complex;

producing an amplified product derived from the hybridized complex; and integrally detecting nondestructive measurement information and genome-related information in the single cell using an expression pattern of the amplified product as an index.

The detection method of the present invention will be described based on preferred embodiments, but the present invention is not particularly limited thereto.

Step of Preparing a Compartment

A step of preparing a compartment of the present invention is a step of preparing a plurality of compartments containing a single cell or a derivative thereof, a first bead(s), and a second bead(s) per compartment. Here, each first bead is a particle cleavably linked to a first barcode nucleic acid corresponding to each imaging information or an organism containing a first barcode nucleic acid corresponding to each imaging information, and imaging information of the first bead(s) in each compartment can be clearly distinguished from each other. The second bead(s) is linked to a plurality of second barcode nucleic acids hybridizable with a genome-related nucleic acid corresponding to a cell genome or an expressed product thereof or the first barcode nucleic acid.

Here, the positional relationship between the cell and the first bead(s) in each compartment is not particularly limited as long as obtaining of nondestructive measurement information of the cell and imaging information of the first bead(s) is not impaired, and it can be appropriately set according to the type, size, and nature of the cell and the first bead(s). In other words, in the present invention, as long as imaging information of both of the cell and the first bead(s) can be obtained, both of them may coexist in a state in which the first bead(s) and the cell are or are not in contact with each other in the same compartment, and the first bead(s) may be introduced into the inside of the cell. Suitable examples of an embodiment in which the first bead(s) and the cell are in contact with each other include an embodiment in which the cell surface and the first bead(s) are directly adhered to each other or the first bead(s) is carried on the cell by using a commercially available cell membrane modifier, or the like. Suitable examples of an embodiment in which the first bead(s) and the cell are not in contact with each other include an embodiment in which the first bead(s) exists without being joined to the cell within the same compartment, or an embodiment in which, by conjugating a subcompartment encompassing the first bead(s) but no cell to the cell, the subcompartment is carried to the cell, or the like. Suitable examples of an embodiment in which the first bead(s) is introduced into the inside of the cell include an embodiment in which the first bead(s) is ingested by the cell, or the like.

The type and the form of a cell to be detected are not particularly limited as long as the effects of the present invention are not impaired, and a cell can be selected according to the object. The above cell contained in the compartment may be a derivative of a cell. Examples of the derivative include a homogenate of a cell, a content of a cell, a lysate of a cell, and a unit composed of a cell (e.g., a cell cluster, a spheroid, an organoid).

The derivative of a cell can be obtained by using a known method such as making a cell coexist with a cell lysis buffer, etc. A step of obtaining, from a cell, a derivative thereof may be performed before both of nondestructive measurement information of a cell and image information of a first bead(s) are obtained and associated and then the cell and the first bead(s) are put in a compartment together with a second bead(s), or the derivative may be produced in a compartment by enclosing together with a cell, first and second bead(s), and a cell lysis buffer.

One embodiment of the step of preparing a compartment of the present invention will be described in accordance with FIG. 1a, but the present invention is not particularly limited thereto.

First, each of a cell group 101 to be detected such as a tissue or a plurality of cells, a plurality of first beads 102, and a plurality of second beads 103 is prepared. In FIG. 1a, the first barcode nucleic acid is an RNA, contains a first common barcode region and polyadenine, and is linked to a first bead via a UV-cleavable linker. The second barcode nucleic acid is an DNA, and contains a PCR primer region, a second common barcode region, a second unique barcode region, and polythymine.

Then, the cell group 101, the plurality of first beads 102, and the plurality of second beads 103 are partitioned to obtain a plurality of compartments 104. By the above partitioning, a combination of a single cell 105 of the above cell group 101, the first bead 102, and the second bead(s) 103 are partitioned into the plurality of compartments 104.

A method for partitioning will be mentioned later.

The number of the above first beads per compartment is not particularly limited, and may be 1, but is preferably plural, more preferably 2 to 100, and still more preferably 2, 3, 4, 5, 6, 7, 8, 9, and 10 in order to increase the number of types of compartments which can be clearly distinguished from each other. Enclosing a plurality of first beads into the compartment at one time enables sudden increase in the number of variations of a combination of imaging information of the first beads in the compartment by a combination of imaging information of a few types of first beads, and enables clear distinction of a large amount of compartments from each other. Here, first beads having the same imaging information also exist, but it is preferable that a plurality of first beads having different types of imaging information exist in the compartment.

For example, an example in which size of the bead, color of fluorescence, and concentration of fluorescence are selected as the imaging information of the first bead(s) will be shown below. It is assumed that the size of the bead includes 3 types (3, 7, and 11 µm), the color of the fluorescent dye includes 3 colors (blue, green, and red), and the intensity level according to the concentration of the fluorescent dye includes 6 types (0, 1, 2, 3, 4, and 5). In this case, the type of the bead will be (intensity level$^{size\ type}$−1)×size type=$(6^3-1)\times3=645$.

Here, when three first beads exist in the compartment, the types of each combination of the first beads are $_{645}C_3 > 10^7$ types, and thus great many types of combinations can be obtained.

The number of the above second beads per compartment is not particularly limited, but is preferably one per compartment in terms of discrimination of genome-related information derived from single cell.

Furthermore, during partitioning, reagents necessary for the subsequent steps, for example, PCR reagents such as a cell lysis buffer and PCR Reaction Mix may be enclosed simultaneously.

Step of Associating Nondestructive Measurement Information of Single Cells with Imaging Information of a Bead A step of associating nondestructive measurement information of a single cell with imaging information of a bead of the present invention includes a step of detecting both nondestructive measurement information of the single cell and imaging information of the first bead(s) and associating the nondestructive measurement information of the single cell with the imaging information of the first bead(s) before preparation of each compartment or in each compartment.

One embodiment of the step of associating nondestructive measurement information of the present invention will be described in accordance with FIG. 1b, but the present invention is not particularly limited thereto.

Both of nondestructive measurement information of the cell 105 in the compartment 104 and imaging information of the first bead(s) 102 are measured. Furthermore, based on the obtained measurement results, the nondestructive measurement information of the cell 105 in the compartment 104 is associated with the imaging information of the first bead(s) 102.

Examples of the above method for detecting or measuring both of nondestructive measurement information of the single cell and imaging information of the first bead(s) include flow cytometry (e.g., an imaging flow cytometry method which observes a compartment flowing in a flow pass, etc.), a microscopic measurement (a method for observing a compartment in a microwell using a general light microscope, etc.) and the like.

According to another embodiment of the present invention, since the compartment 104 can be identified by imaging information of a bead, for example, after a given time elapsed after incubation, chemical assay, or obtaining imaging information or nondestructive measurement information of a cell, e.g., 10 minutes after, it is also possible to measure nondestructive measurement information of the cell, etc., again.

Here, the above imaging information of the first bead(s) is not particularly limited as long as imaging information of the first bead(s) in each compartment can be clearly distinguished from each other, and the imaging information may be imaging information possessed by the bead itself or imaging information imparted by labeling. Here, "imaging" encompasses a method which can separate and measure the measurement information of a test subject such as a bead, which temporally overlaps based on spatial information. Measurement information of a test subject obtained by the above imaging is referred to as imaging information. Examples of the above imaging information include at least one piece of measurement information selected from color, fluorescence, size, shape, electromagnetic wave, transmission, phase, scattering, reflection, coherent Raman, infrared spectroscopy, Raman spectroscopy, absorption spectrum, and the number of first beads. The imaging information is preferably infrared spectroscopy imaging, Raman spectroscopy imaging, color imaging, and fluorescence imaging.

The fluorescence can be obtained by organic fluorescent molecules, organism-derived fluorescent molecules, quantum dots, inorganic substances such as heavy metals, or a combination thereof.

Measurement information such as transmission, phase, scattering, and reflection can be obtained by organic substances or inorganic substances having a different refractive index or color depending on the concentration or a combination thereof. These types of information can be obtained by a bright field observation method, etc.

Absorption spectrum and Raman can be obtained by organic molecules or inorganic substances having a different absorption wavelength range (molecular footprint) having absorption and Raman scattering spectra or a combination thereof, and examples thereof include alkyne-based compounds having a wavelength range which does not overlap with a cell signal.

Coherent Raman can be measured by, for example, the coherent anti-Stokes Raman scattering (CARS) method or the stimulated Raman scattering (SRS) method.

The size, color, and shape of a bead also become imaging information of the first bead(s), and these size, color, and shape can be diverse by forming the bead by, for example, flow lithography. These types of information can be obtained by a bright field observation method, etc.

Since imaging information of a bead is spatially separated from a cell, it can be separated without interfering with nondestructive measurement information of the cell.

Furthermore, the above nondestructive measurement information of a cell is not particularly limited as long as the feature of the cell can be recognized, examples thereof include imaging information, morphological information obtained from the cell, measurement information of a physical wave (e.g., sound, ultrasonic wave) obtained from the cell, and measurement information of an electromagnetic wave (e.g., light, terahertz) obtained from the cell. Here, the above imaging information can be obtained in the same manner as for imaging information of the first bead(s). Examples of the above nondestructive measurement information include imaging information based on measurement information such as color, fluorescence, size, shape, electromagnetic wave, transmission, phase, scattering, reflection, coherent Raman, infrared spectroscopy, Raman, or absorption spectrum, or morphological information of a cell such as nucleus, size of the cytoplasm, coarseness and fineness of the cytoskeleton, feature amount of the internal structure, uniformity of the membrane, fluorescence intensity of each structure, molecular localization, or positional relationship of the molecule or the subject to be observed, and the nondestructive measurement information is preferably morphological information obtained from the cell.

Figure 1C:
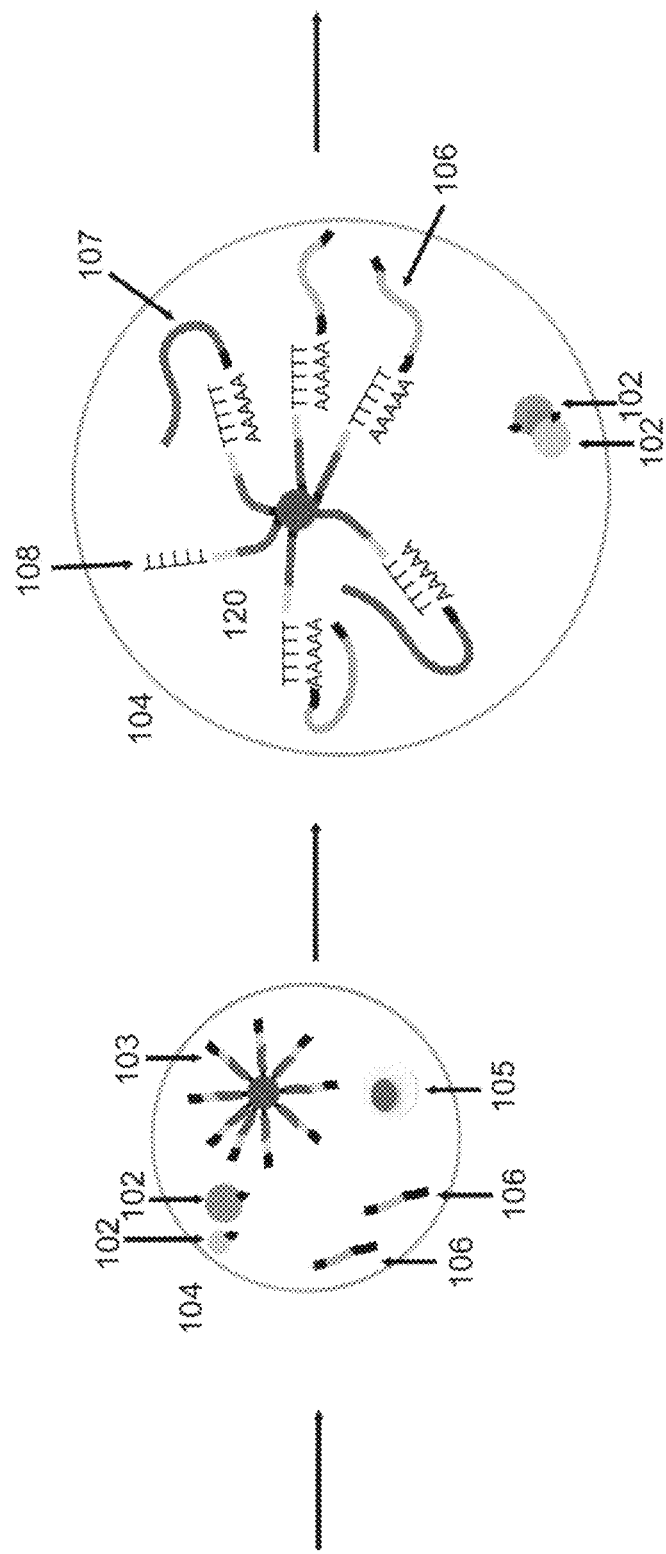
Figure 1D:
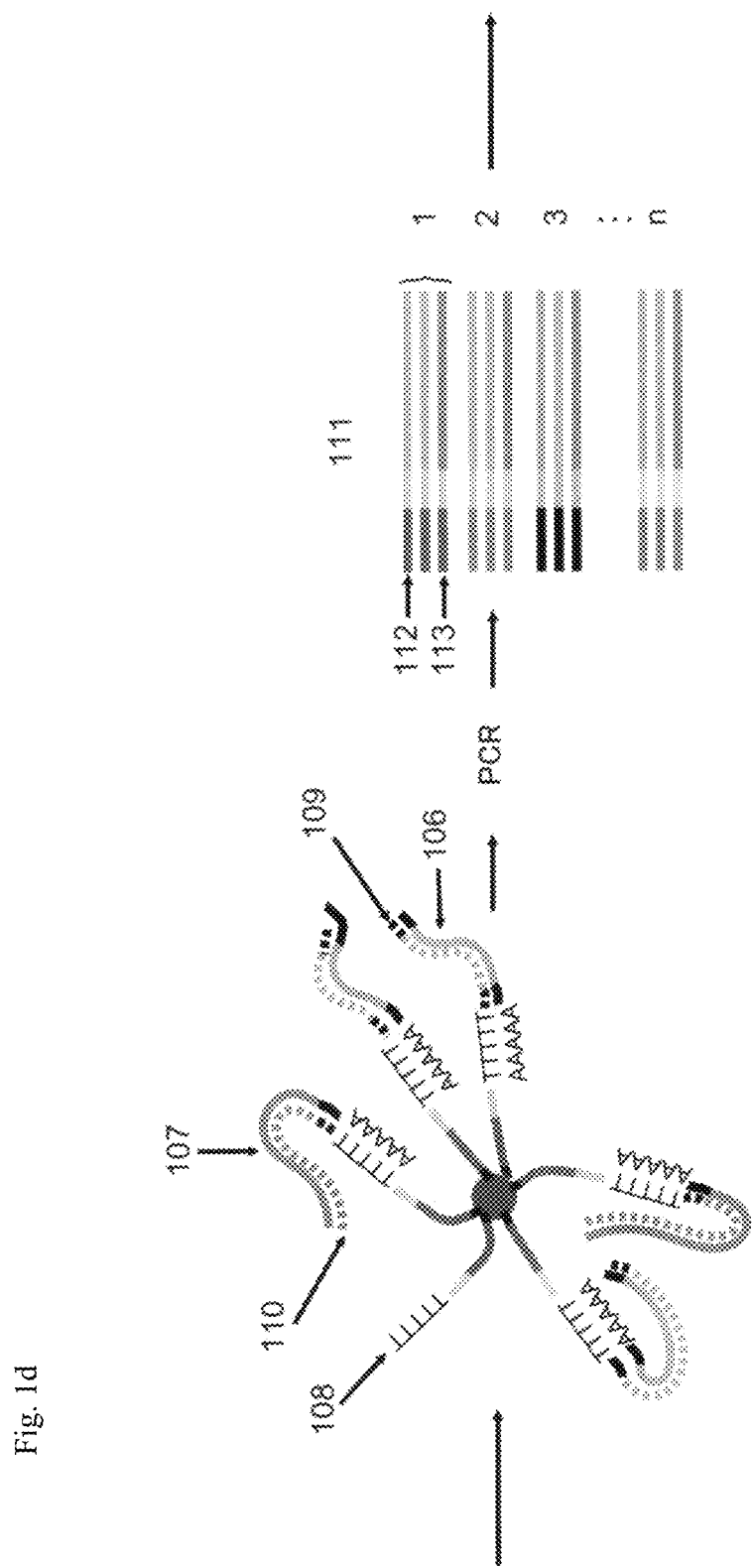
Figure 1E:
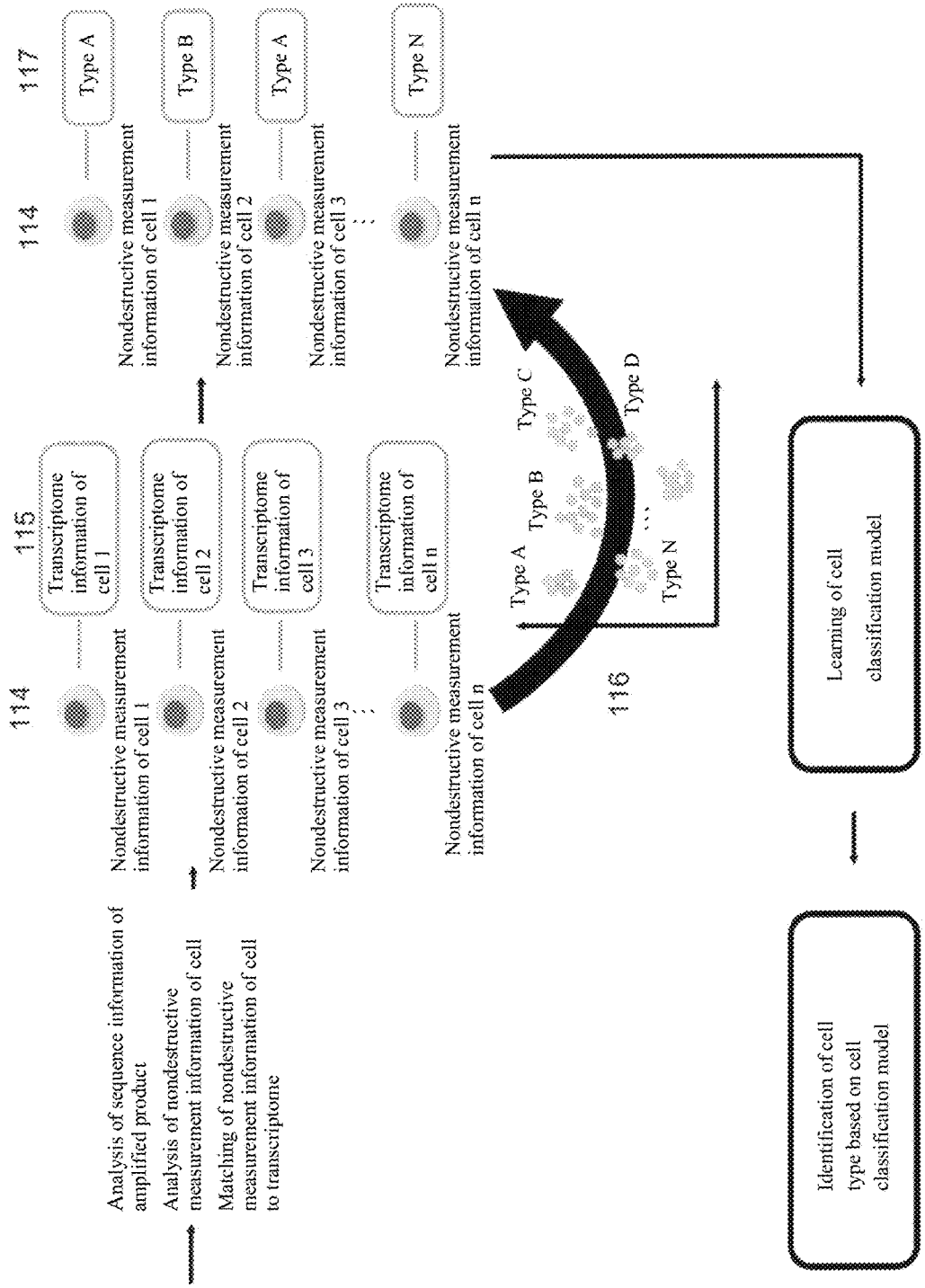
Figure 1F:
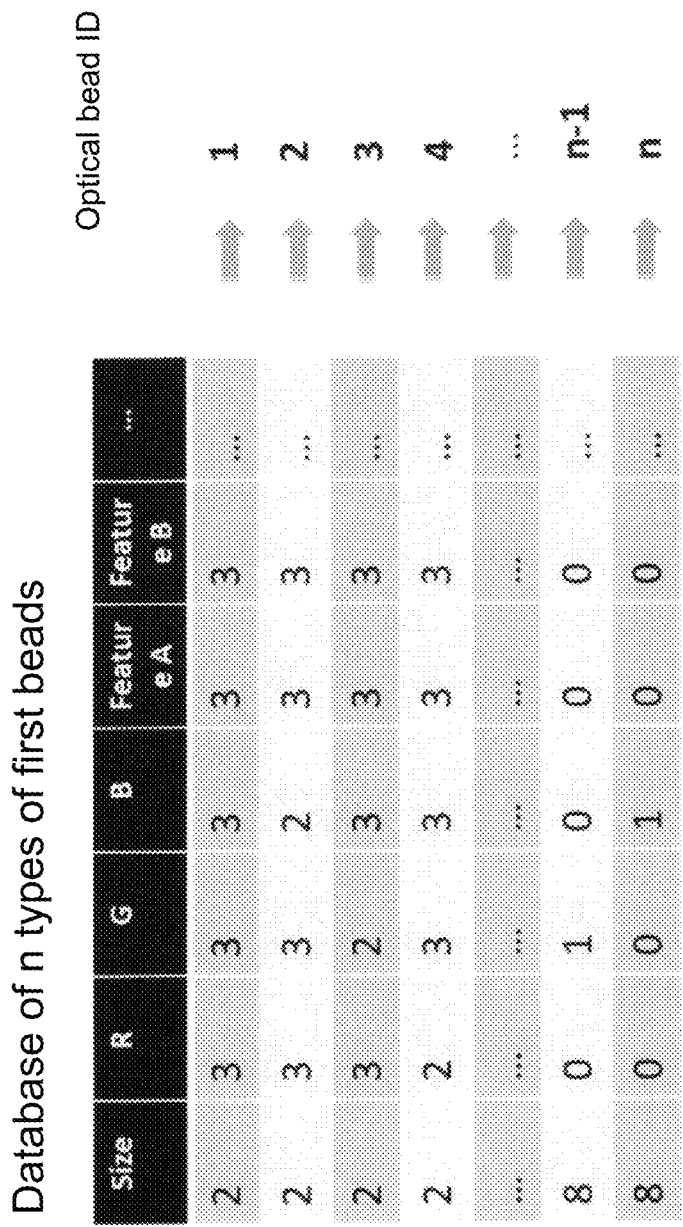
Figure 1G:
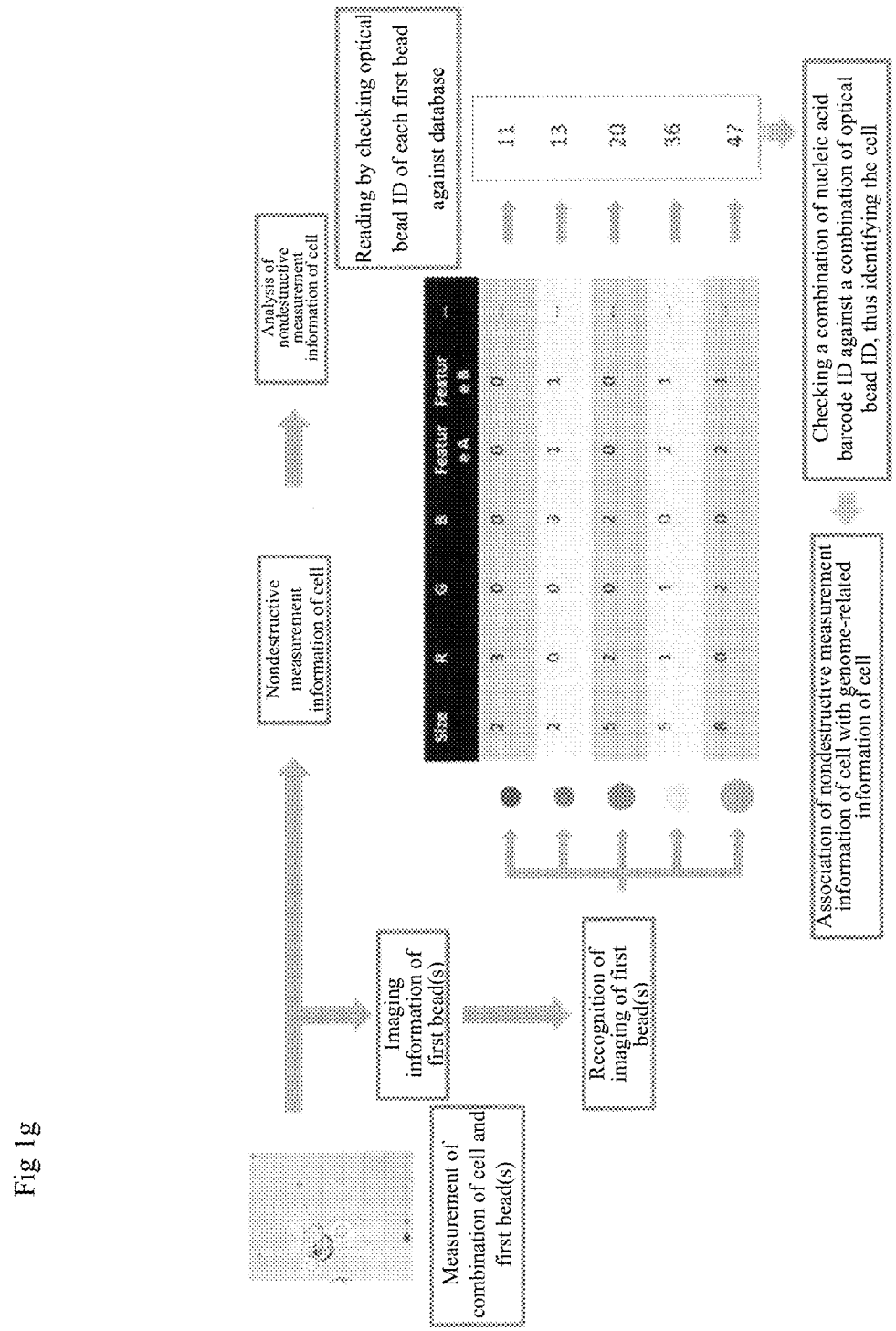

In FIG. 1f and FIG. 1g, an analytical scheme of imaging information will be more specifically described as an example.

FIG. 1f is a schematic diagram of a database of the first bead(s) when imaging information of n types (ID) of beads produced by controlling the size, RGB, fluorescent brightness, and other optical properties is used as an index. In FIG. 1f, imaging information of the first bead(s) is measured, and an optical bead ID is linked to the imaging information of the first bead(s) thus obtained.

Furthermore, in FIG. 1g, a combination of a cell and a first bead(s) is measured, and nondestructive measurement information of the cell is associated with imaging information of the first bead(s). First, the optical barcode ID of each first bead is read (here, optical calibration is performed). To each first bead, a nucleic acid barcode ID is imparted based on the first common barcode region of the first barcode nucleic acid linked to the first bead(s). Therefore, a combination of the above nucleic acid barcode ID of the first bead(s) is checked against a combination of the above optical bead ID to identify the cell. Subsequently, nondestructive measurement information of the cell can be linked to genome-related information of the cell.

The step of associating nondestructive measurement information of single cells with imaging information of the first bead(s) of the present invention may be performed before preparation of each compartment or after preparation of each compartment. Particularly, in an embodiment in which both nondestructive measurement information of single cells and imaging information of the first bead(s) are detected and associated before preparation of each compartment, it is preferable that, after the association, the cell is lysed or crushed to obtain a derivative of the cell, a mixture of the derivative and the first bead(s) is enclosed into the compartment together with the second bead(s), and a subsequent step of obtaining a hybridized complex is performed.

Here, the positional relationship between the cell and the first bead(s) in the embodiment in which both nondestructive measurement information of single cells and imaging information of the first bead(s) are detected and associated before preparation of each compartment is the same as the above positional relationship between the cell and the first bead(s) in each compartment, and is not particularly limited as long as obtaining of nondestructive measurement information of the cell and imaging information of the first bead(s) is not impaired, and it can be appropriately set according to the type, size, and nature of the cell and the first bead(s). In other words, in the present invention, as long as both nondestructive measurement information of the cell and imaging information of the first bead(s) can be obtained, both of them may coexist in a state in which the first bead(s) and the cell are or are not in contact with each other in the same compartment, and the first bead(s) may be introduced into the inside of the cell. Suitable examples include, for example, an embodiment in which the first bead(s) is carried on the cell, an embodiment in which, by conjugating a subcompartment encompassing the first bead(s) but no cell to the cell, the subcompartment is carried to the cell, an embodiment in which the first bead(s) is ingested by the cell, or the like.

Step of Obtaining a Hybridized Complex

A step of obtaining a hybridized complex includes a step of cleaving the first barcode nucleic acid from the associated first bead(s), and hybridizing each of the genome-related nucleic acid and the first barcode nucleic acid with the second barcode nucleic acid to obtain a hybridized complex.

The above step can be performed by a known method. For example, the above step can be performed by the method mentioned in E. Z. Macosko et al., Highly Parallel Genome-wide Expression Profiling of Individual Cells Using Nano-liter Droplets. Cell. 161, 1202-1214 (2015).

One embodiment of the step of obtaining a hybridized complex will be described in accordance with FIG. 1c, without particular limitation.

Subsequent to the above step of associating nondestructive measurement information of the single cell with imaging information of a bead, the cleavable linker is cleaved (for example, a UV-cleavable linker is cleaved by UV irradiation), the first barcode nucleic acid 106 is separated, and then the cell is lysed. Then, in the compartment, each of the cell-derived mRNA 107 and the first barcode nucleic acid 106 derived from the first bead(s) is hybridized with the second barcode nucleic acid 108 to obtain a hybridized complex 120. Then, the droplet is destroyed.

Step of Producing an Amplified Product Derived from the Hybridized Complex

A step of producing an amplified product derived from the hybridized complex includes a step of producing an amplified product derived from the hybridized complex obtained in the above step of obtaining a hybridized complex.

The above step can be performed by a known method. For example, the above step can be performed by the method mentioned in E. Z. Macosko et al., Highly Parallel Genome-wide Expression Profiling of Individual Cells Using Nano-liter Droplets. Cell. 161, 1202-1214 (2015).

One embodiment of the step of producing an amplified product derived from the hybridized complex will be described in accordance with FIG. 1d, without particular limitation.

A reverse transcription is performed for the hybridized complex obtained in the above step of obtaining a hybridized complex. By this reverse transcription, a cDNA 110 for the cell-derived mRNA 107 is synthesized, and a cDNA 109 for the first barcode nucleic acid 106 is synthesized. Then, template switching may be performed.

Then, a PCR reaction is performed. This PCR reaction produces two types of amplified products 111 including a first amplified product 112 derived from the hybridized complex of the first barcode nucleic acid 106 with the second barcode nucleic acid 108 and a second amplified product 113 derived from the hybridized complex of the cell-derived mRNA 107 and the second barcode nucleic acid 108. When the genome-related nucleic acid is a DNA, an extension PCR method can be performed as the above PCR reaction.

Then, based on the amplified product thus obtained, a library of amplified products including the first amplified product and the second amplified product derived from each of 1 to n compartments is prepared.

Step of Integrally Detecting Nondestructive Measurement Information and Genome-Related Information in Single Cells A step of integrally detecting nondestructive measurement information and genome-related information in a single cell include a step of integrally detecting nondestructive measurement information and genome-related information in a single cell using, as an index, an expression pattern of the amplified product obtained in the above step of producing an amplified product derived from the hybridized complex. Examples of the above expression pattern of the amplified product include sequence information of the amplified product, or, in the sequence information, sequence information of the first barcode nucleic acid, sequence information of the first common barcode region, sequence information of the first unique barcode region, sequence information of the second barcode nucleic acid, sequence information of the second common barcode region, or sequence information of the second unique barcode region or the like obtained by sequencing.

One embodiment of the step of integrally detecting nondestructive measurement information and genome-related information in a single cell will be described in accordance with FIG. 1e, without particular limitation.

The sequence of the amplified products (the first amplified product and the second amplified product) obtained in the above step of producing an amplified product derived from the hybridized complex is determined by a sequencer, and sequence information of the amplified products is analyzed. In the analysis of the second amplified product, a cell from which each amplified product is derived is assigned using sequence information of the second common barcode region as an index. Since each mRNA molecule can be discriminated by sequence information of the second unique barcode region, information such as the sequence of an mRNA for each cell and the expression amount thereof and the like can be obtained using the sequence information as an index. Based on the information obtained by the above analysis of the second amplified product, transcriptome information 115 for each cell can be obtained.

Next, nondestructive measurement information 114 of a cell is analyzed. Here, as mentioned above, nondestructive measurement information of the single cell is associated with imaging information of the first bead(s), and a first barcode nucleic acid corresponding to each imaging information is linked to the first bead(s). Therefore, in the above analysis, based on sequence information of the first common barcode region of the first barcode nucleic acid, nondestructive measurement information 114 of a cell from which each first amplified product is derived can be assigned to each first amplified product.

Next, nondestructive measurement information 114 of a cell is matched to transcriptome information 115. Therefore, one-to-one linking is possible between genome-related information and nondestructive measurement information of the single cell in each compartment.

Furthermore, it is possible to provide a method for analyzing, discriminating, or classifying a test cell, based on nondestructive measurement information in the test cell, using a classification model obtained based on the nondestructive measurement information and the genome-related information in the single cell obtained above.

In the above method, first, it is possible to produce a database of nondestructive measurement information and genome-related information of the single cell. Furthermore, using the above database, it is possible to label each cell with several types 117 (cell types A, B, C, ... N) and classify by performing clustering 116 of genome-related information, based on the results of matching of the above nondestructive measurement of the single cell to genome-related information of transcriptome, etc., of the cell. Using the above nondestructive measurement information of the single cell and the cell classification results thus obtained as teaching data, it is possible to obtain a classification model by performing machine learning on nondestructive measurement information in the single cell (supervised machine learning).

Furthermore, using the classification model obtained above, it is possible to analyze, discriminate, or classify a test cell, based on nondestructive measurement information in the test cell. For example, it is possible to identify a cell type clustered by genome-related information on the cell, based on the above nondestructive measurement information of the test cell.

As another embodiment of the above method for analyzing, discriminating, or classifying a test cell, the following method is also exemplified.

First, it is possible to produce a database of nondestructive measurement information and genome-related information of single cells. Using the above database, it is possible to label each cell with several types (cell types A, B, C, ... N) and classify by performing clustering of nondestructive measurement information, based on the results of matching of the above nondestructive measurement of the single cell to genome-related information of transcriptome, etc., of the cell. Using the above nondestructive measurement information of the single cell and the cell classification results thus obtained as teaching data, it is possible to obtain a classification model by performing machine learning on genome-related information in the single cell (supervised machine learning).

Furthermore, using the classification model obtained above, it is possible to analyze, discriminate, or classify a test cell, based on genome-related information in the test cell.

The first bead(s), the second bead(s) and the like as used herein will be described below.

First Bead(s) Which is Cleavably Linked to a First Barcode Nucleic Acid and Which Has Imaging Information That Can Be Clearly Distinguished from Each Other FIG. 2 shows an embodiment in which the first barcode nucleic acid is an RNA as one embodiment of a first bead(s) which is cleavably linked to a first barcode nucleic acid and which has imaging information that can be clearly distinguished from each other (hereinafter also referred to as first bead(s) linked to a first barcode nucleic acid).

A first barcode nucleic acid 202 is linked to a first bead 201 having imaging information that can be clearly distinguished from each other. The first barcode nucleic acid 202 contains a first common barcode region 203 and a first hybridize region 204. The first barcode nucleic acid 202 contains the first common barcode region 203 and the first hybridize region 204 in this order from the first bead side. Here, an example of the first hybridize region 204 includes polyadenine. Furthermore, the first barcode nucleic acid 202 is cleavably linked to the first bead 201 via a cleavable linker 205.

Organism Containing a First Barcode Nucleic Acid

The first bead(s) of the present invention may be an organism(s) containing a first barcode nucleic acid and having imaging information that can be clearly distinguished from each other (hereinafter also referred to as organism containing a first barcode nucleic acid).

The organism(s) preferably contains a plasmid having a first barcode nucleic acid. Imaging information in the organism(s) is not particularly limited as long as it is imaging information of the present invention, but it is preferably the number of organisms or fluorescence. Examples of the fluorescence include not only a spectrum of each color but also brightness information thereof. Furthermore, fluorescence is preferably obtained from a fluorescent protein expressed from a fluorescent protein gene existing in a plasmid. Therefore, the organism(s) of the present invention preferably contains, for example, a plasmid having a first barcode nucleic acid and a fluorescent protein gene. Here, the first barcode nucleic acid contains a first common barcode region (e.g., a common barcode region common for each fluorescent protein) and a first hybridize region, and examples of the first hybridize region include polyadenine. Furthermore, the first barcode nucleic acid may contain a third unique barcode region. The third unique barcode region enables clear distinction of each clone of an organism(s). Therefore, the constitution of a plasmid in the organism(s) of the present invention is regarded, for example, to include a fluorescent protein gene region, a third unique barcode region, a first common barcode region, and a first hybridize region in this order.

First Bead(s)

The first bead(s) of the present invention is a bead that can be clearly distinguished from each other by imaging information.

In the present description, the bead is not particularly limited as long as it is a particle to which a barcode nucleic acid can be linked or an organism which can contain a barcode nucleic acid, and the shape is not limited.

When the first bead(s) is a particle(s), the material thereof is not particularly limited, and examples thereof include a semiconductor such as a quantum dot (semiconductor nanoparticle) made of a semiconductor material such as cadmium selenide (CdSe), zinc sulfide (ZnS), cadmium sulfide (CdS), zinc selenide (ZnSe), or zinc oxide (ZnO); an inorganic substance such as a heavy metal such as gold; a hydrogel such as acrylamide, agarose, collagen, alginic acid, or PEG-based; a resin such as polystyrene, polypropylene, or a hydrophilic vinyl polymer (e.g., Toyopearl HW-65S (Tosoh Corporation)); or a hydrophilic vinyl polymer to which PEG or a derivative thereof is bound, or the like, and it is preferably a hydrogel, and more preferably acrylamide or alginic acid.

When the first bead(s) is an organism(s), the type and the form of the organism(s) are not particularly limited as long as the effects of the present invention are not impaired, and an organism(s) can be selected according to the object. Examples of the organism(s) include a eukaryote or a prokaryote or a cell thereof, and, for example, a microorganism, etc., and specific examples thereof include a bacterium such as *Escherichia coli* or a fungus such as yeast. The organism(s) is preferably capable of amplifying a plasmid containing a first barcode nucleic acid.

First Barcode Nucleic Acid

The first barcode nucleic acid of the present invention is not particularly limited as long as it contains a barcode region corresponding to each imaging information, and for example, the nucleic acid is an RNA, a DNA, or a combination thereof.

Each first barcode nucleic acid of the present invention preferably includes a first common barcode region which is common in the first bead(s) corresponding to same imaging information and a first hybridize region hybridizable with the second barcode nucleic acid. By using sequence information of the first common barcode region, one-to-one correspondence is possible to imaging information of the first bead(s) having the same imaging information in each compartment. Therefore, association can make an index of identifying nondestructive measurement information of a single cell existing in the same compartment.

It is preferable that a plurality of the above first barcode nucleic acids are linked to one first bead.

It is preferable that one type of the first barcode nucleic acid is linked to the first bead(s) of the present invention.

The first barcode nucleic acid can be directly or indirectly linked to the first bead(s). The first barcode nucleic acid is preferably cleavably linked to the first bead(s), and, for example, can be linked via a cleavable linker. In the present invention, examples of the cleavable linker include a chemically cleavable linker, a photocleavable linker such as UV-cleavable linker, a thermologically cleavable linker, an enzymatically cleavable linker or the like. By using the above linker, it is shown that the linked nucleic acid is cleaved from the bead, and can be separated or released. Examples of such a linker include PC-biotin, iSpPC or the like as a photocleavable linker or a disulfide bond or the like as a chemically cleavable linker.

As another preferred embodiment of the first bead(s) of the present invention, the first bead(s) may further contain a first unique barcode region and a primer region each of which can be clearly distinguished from each other. As further another preferred embodiment of the first bead(s) of the present invention, the first bead(s) may have an acrylamide moiety such as an acrylic phosphoramidite moiety (Acrydite (trademark)) via a cleavable linker.

Method for Producing a First Bead(s) Which is Cleavably Linked to a First Barcode Nucleic Acid and Which Has Imaging Information That Can Be Clearly Distinguished from Each Other A method for producing a first bead(s) linked to a first barcode nucleic acid can be performed according to a known method. For example, production can be performed according to the method mentioned in A. M. Klein et al., Droplet Barcoding for Single-Cell Transcriptomics Applied to Embryonic Stem Cells. Cell. 161, 1187-1201 (2015).

As an example of the above method, by microfluidic emulsion technology, an aqueous first barcode nucleic acid-containing acrylamide:bisacrylamide solution is made to be an acrylamide polymer in an organic solvent layer, and this is used as the first bead(s). Here, the bead-linked side of a cleavable linker bound to a first barcode nucleic acid can be modified by an acrylamide moiety such as an acrylic phosphoramidite moiety (Acrydite (trademark)). By the above modification, the first barcode nucleic acid is also polymerized into an acrylamide polymer during polymerization of acrylamide. Before this emulsification, for example, by dissolving a fluorescence-labeled acrylamide monomer in the above aqueous solution, it is possible to produce first beads having various fluorescence intensities of each color. Specifically, the first bead(s) can be produced by a droplet production method using a flow focusing device or microfluidic techniques such as a microwell. The size of the bead can be controlled by changing the fluidic conditions for the flow focusing device and by changing the size of each chamber for the microwell. After polymerization, the first bead(s) thus obtained is removed from the droplet and washed several times, and this is used as the first bead(s).

With respect to the method for producing a first bead(s) linked to a first barcode nucleic acid, production can also be performed by a known method. For example, production can be performed by the method mentioned in JP 2009-513948 T or JP 2017-506877 T.

An example of the above method will be described. First, for the first barcode nucleic acid, a particular nucleic acid sequence is prepared by a solid-phase synthesis method or an enzyme synthesis method. Then, it is bound to the first bead(s) via a cleavable linker. When the barcode nucleic acid is an RNA, a DNA template, which becomes a complementary strand of a single-stranded barcode nucleic acid, is synthesized, and then synthesis may be performed by a linear amplification reaction using an RNA polymerase such as T7, which binds to a promoter sequence on the DNA template to synthesize an RNA containing a single-stranded barcode region.

Second Bead(s) Linked to a Plurality of Second Barcode Nucleic Acids

FIG. 3 shows one embodiment in which a second bead(s) linked to a plurality of second barcode nucleic acids hybridizable with a genome-related nucleic acid and a first barcode nucleic acid (hereinafter also referred to as second bead(s) linked to a second barcode nucleic acid).

In FIG. 3, a second barcode nucleic acid 302 is linked to a second bead 301. The second barcode nucleic acid 302 contains a second common barcode region 303, a second unique barcode region 304, and a second hybridize region 305. The second barcode nucleic acid 302 contains a PCR primer region 306, the second common barcode region 303, the second unique barcode region 304, and the second hybridize region 305 in this order from the second bead side. The above second hybridize region 305 is polythymine.

The second bead(s) is preferably linked to 1,000 to 100,000 second barcode nucleic acids in terms of the fact that it can be hybridized with many genome-related nucleic acids.

Second Bead(s)

As the material of the second bead(s) of the present invention, the same material as for the first bead particle(s) can be used.

The material of the second bead(s) of the present invention is preferably a hydrogel or a resin, and more preferably acrylamide, polystyrene, a hydrophilic vinyl polymer, PEG, or a hydrophilic vinyl polymer to which a derivative thereof is bound.

Second Barcode Nucleic Acid

The second barcode nucleic acid of the present invention is not particularly limited as long as it contains a barcode region, and for example, the nucleic acid is an RNA, a DNA, or a combination thereof. The second barcode nucleic acid can be directly or indirectly linked to the second bead(s).

The second barcode nucleic acid of the present invention preferably contains a second common barcode region which is in common with each other, a second unique barcode region which can be clearly distinguished from each other, and a second hybridize region. Here, sequence information of the above second common barcode region can be used as an index of identifying a cell existing together with the second barcode nucleic acid in a compartment. Furthermore, sequence information of the above second unique barcode region can be used as an index of identifying a genome-related nucleic acid. The above second hybridize region can be hybridized with each of the genome-related nucleic acid and the first barcode nucleic acid. Therefore, the second hybridize region preferably contains polythymine or a nucleic acid complementary to the genome-related nucleic acid.

As mentioned above, since the genome-related nucleic acid is associated with sequence information of the above second common barcode region, it is possible to identify a cell from which the genome-related nucleic acid is derived. Furthermore, since the above second barcode nucleic acid is hybridized with the first barcode nucleic acid, sequence information of the first common barcode region, etc., of the first bead(s) is also associated with sequence information of the above second common barcode region. Sequence information of the first common barcode region is associated with imaging information of each first bead. Nondestructive measurement information of the cell is also associated with imaging information of each first bead. Therefore, one-to-one correspondence is possible to genome-related nucleic acid information and nondestructive measurement information of the cell.

Figure 4:
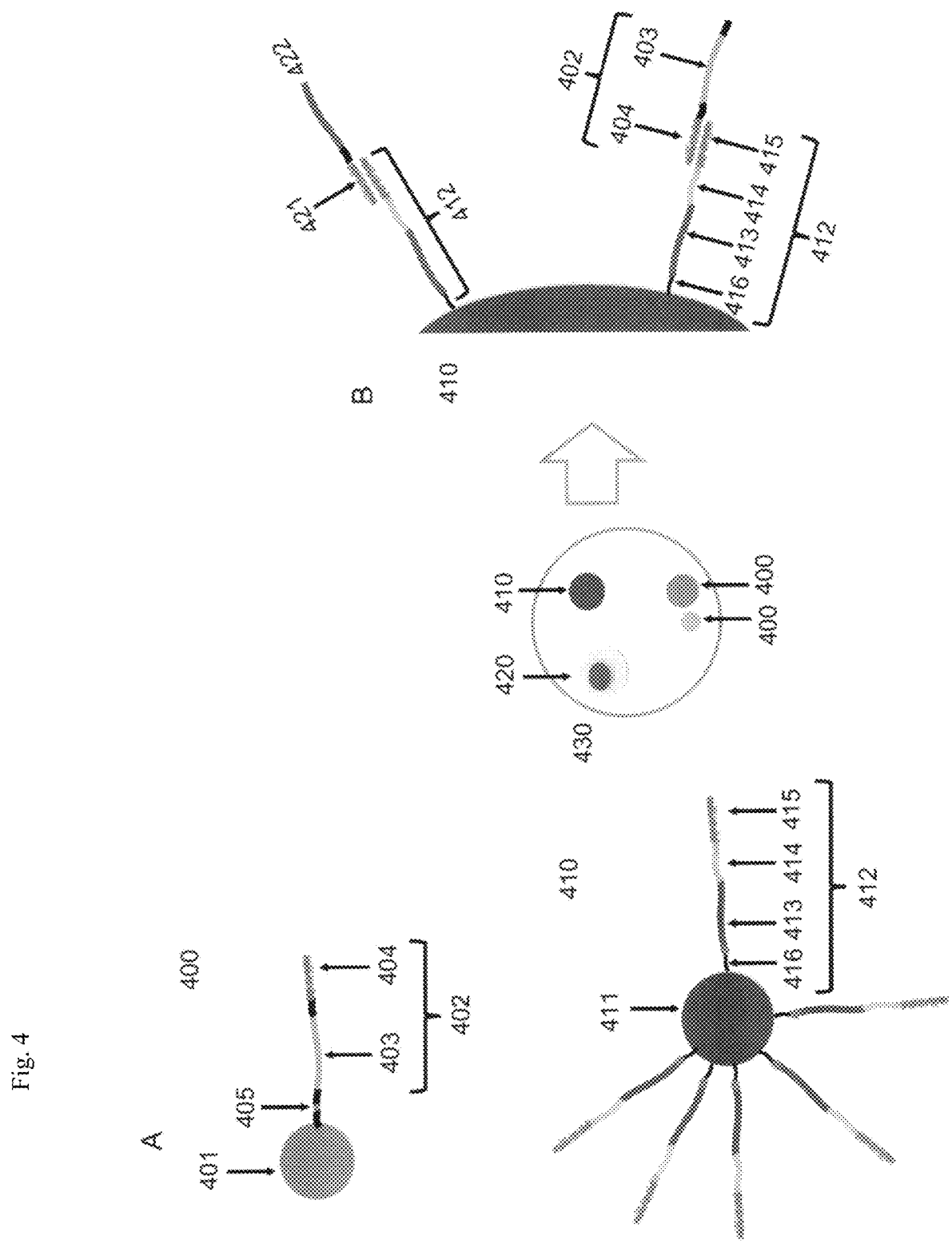
FIG. 4 is a schematic diagram showing another embodiment of the first bead(s) linked to the first barcode nucleic acid and the second bead(s) linked to the second barcode nucleic acid of the present invention.

Furthermore, another embodiment of the first bead(s) linked to the first barcode nucleic acid and the second bead(s) linked to the second barcode nucleic acid is shown in FIG. 4. FIG. 4 shows, as another embodiment, an embodiment in which each of the first barcode nucleic acid and the second barcode nucleic acid is a DNA.

In a first bead(s) linked to a first barcode nucleic acid 400 in FIG. 4A, a first barcode nucleic acid 402 is linked to a first bead(s) 401 having imaging information that can be clearly distinguished from each other. The first barcode nucleic acid 402 contains a first common barcode region 403 and a first hybridize region 404. The first barcode nucleic acid 402 contains the first common barcode region 403 and the first hybridize region 404 in this order from the first bead side. Furthermore, the first barcode nucleic acid 402 is cleavably linked to the first bead(s) 401 via a cleavable linker 405. Furthermore, the first hybridize region 404 is a sequence complementary to the second hybridize region 415 mentioned below.

In a second bead linked to a second barcode nucleic acid 410 in FIG. 4A, a second barcode nucleic acid 412 is linked to a second bead 411. The second barcode nucleic acid 412 contains a second common barcode region 413, a second unique barcode region 414, and a second hybridize region 415. The second barcode nucleic acid 412 contains a PCR primer region 416, the second common barcode region 413, the second unique barcode region 414, and the second hybridize region 415 in this order from the second bead side. The above second hybridize region 415 is a sequence which is hybridized with a particular sequence of a genome-related nucleic acid 422 and is complementary to the sequence.

Furthermore, FIG. 4A shows a compartment 430 containing a cell 420 together with the first bead(s) linked to a first barcode nucleic acid 400 and the second bead linked to a second barcode nucleic acid 410.

FIG. 4B shows a hybridized complex. Here, the second barcode nucleic acid 412 is hybridized with a first hybridize region 404 of a first barcode nucleic acid 402 in a second hybridize region 415. Furthermore, the second barcode nucleic acid 412 is hybridized with a particular sequence 421 of a genome-related nucleic acid 422 in the second hybridize region 415.

Figure 5:
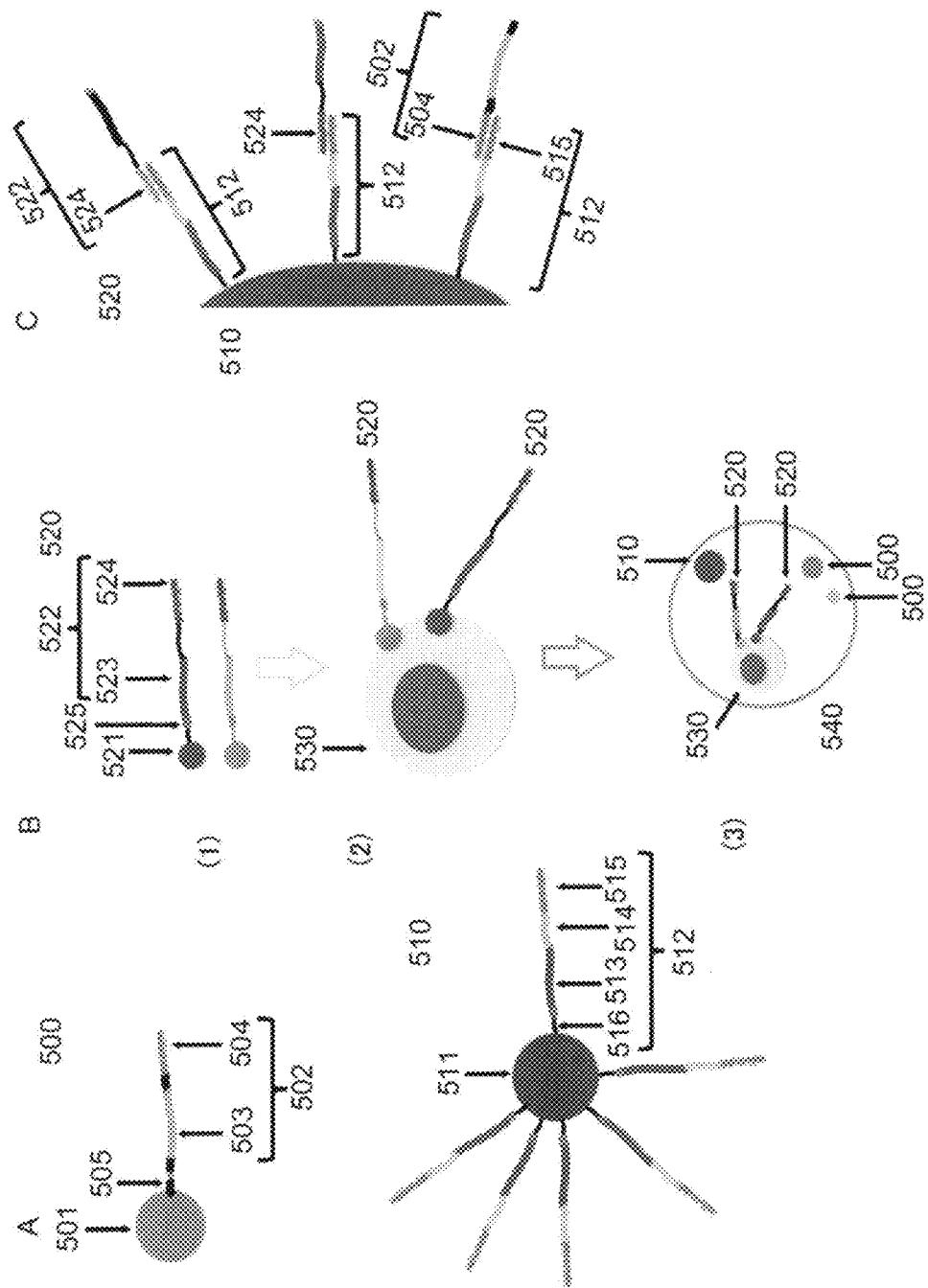
FIG. 5 is a schematic diagram showing further another embodiment of the first bead(s) linked to the first barcode nucleic acid and the second bead(s) linked to the second barcode nucleic acid of the present invention.

Furthermore, further another embodiment of the first bead(s) linked to the first barcode nucleic acid and the second bead(s) linked to the second barcode nucleic acid is shown in FIG. 5. FIG. 5 shows an embodiment in which each of the first barcode nucleic acid and the second barcode nucleic acid is a DNA and a nucleic acid probe 520 which is specific to a molecule such as a protein expressed in one cell (hereinafter also referred to as nucleic acid probe 520) is included.

In a first bead(s) linked to a first barcode nucleic acid 500 in FIG. 5A, a first barcode nucleic acid 502 is linked to a first bead(s) 501 having imaging information that can be clearly distinguished from each other. The first barcode nucleic acid 502 contains a first common barcode region 503 and a first hybridize region 504. The first barcode nucleic acid 502 contains the first common barcode region 503 and the first hybridize region 504 in this order from the first bead side. Furthermore, the first barcode nucleic acid 502 is cleavably linked to the first bead 501 via a cleavable linker 505. Furthermore, the first hybridize region 504 is a sequence complementary to the second hybridize region 515 mentioned below.

In a second bead linked to a second barcode nucleic acid 510 in FIG. 5A, a second barcode nucleic acid 512 is linked to a second bead 511. The second barcode nucleic acid 512 contains a second common barcode region 513, a second unique barcode region 514, and a second hybridize region 515. The second barcode nucleic acid 512 contains a PCR primer region 516, the second common barcode region 513, the second unique barcode region 514, and the second hybridize region 515 in this order from the second bead side. The above second hybridize region 515 is a sequence complementary to a hybridize region 524 of a nucleic acid probe 520.

FIG. 5B(1) shows the nucleic acid probe 520. FIG. 5B(2) shows an embodiment in which the nucleic acid probe 520 is bound to a protein expressed in the cell 530, which was obtained by mixing the above nucleic acid probe 520 with a cell 530 and washing. Furthermore, FIG. 5B(3) shows a compartment 540 containing a cell 530 to which the above nucleic acid probe 520 is bound together with the first bead linked to a first barcode nucleic acid 500 and the second bead linked to a second barcode nucleic acid 510.

In the nucleic acid probe 520 in FIG. 5B(1), a third barcode nucleic acid 522 is linked to a molecule 521 which binds specifically to a molecule such as a target protein expressed in a single cell (hereinafter also referred to as binding molecule 521). The third barcode nucleic acid 522 contains a third common barcode region 523 and a third hybridize region 524. The third barcode nucleic acid 522 contains the third common barcode region 523 and the third hybridize region 524 in this order from the binding molecule 521. Furthermore, the third barcode nucleic acid 522 is cleavably linked to the binding molecule 521 via a cleavable linker 525. Furthermore, the third hybridize region 524 is a sequence complementary to the second hybridize region 515. The above nucleic acid probe 520 may be plural types of probes containing a third barcode nucleic acid 522 different for each binding molecule 521.

FIG. 5C shows a hybridized complex. The second barcode nucleic acid 512 is hybridized with a first hybridize region 504 of a first barcode nucleic acid 502 in a second hybridize region 515. Furthermore, the second barcode nucleic acid 512 is hybridized with a third hybridize region 524 of a third barcode nucleic acid 522 in the second hybridize region 515.

Analysis of sequence information of an amplified product derived from the sequence of the third common barcode region 523 of the above nucleic acid probe 520 enables confirmation of the presence or absence of expression or the amount of expression of a target molecule in a cell.

Therefore, use of a nucleic acid probe specific to a molecule expressed in a single cell enables one-to-one correspondence between a large amount of proteomics and nondestructive measurement information of a cell.

Figure 6:
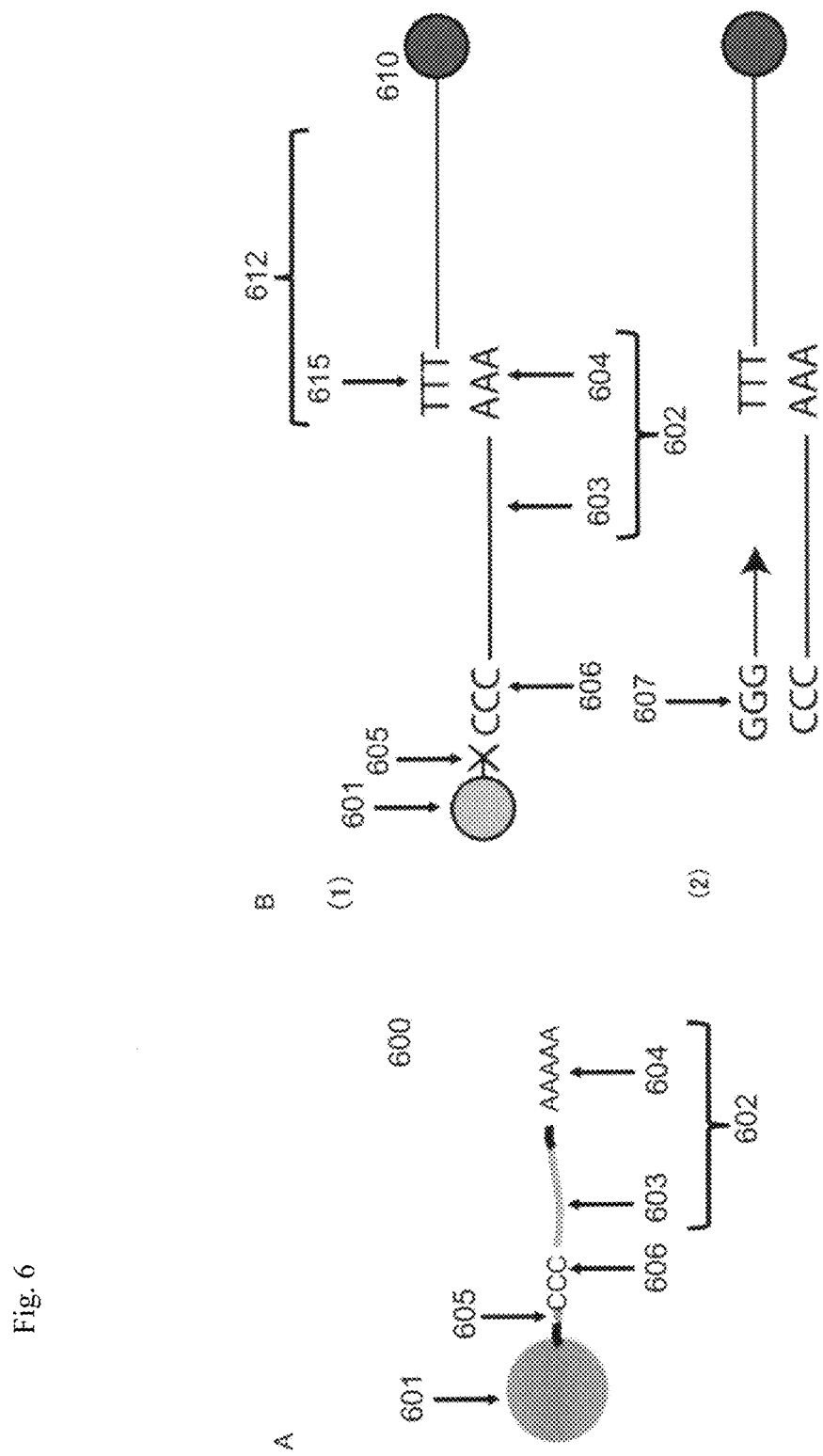
FIG. 6 is a schematic diagram showing another embodiment of the first bead(s) linked to the first barcode nucleic acid of the present invention.

Furthermore, another embodiment of the first bead(s) linked to the first barcode nucleic acid is shown in FIG. 6. FIG. 6 shows, as another embodiment, an embodiment in which the first barcode nucleic acid is a DNA and contains a particular sequence.

In a first bead linked to a first barcode nucleic acid 600 in FIG. 6A, a first barcode nucleic acid 602 is linked to a first bead 601 having imaging information that can be clearly distinguished from each other. The first barcode nucleic acid 602 contains a first common barcode region 603 and a first hybridize region 604. The first barcode nucleic acid 602 contains the first common barcode region 603 and the first hybridize region 604 in this order from the first bead side. Furthermore, the first barcode nucleic acid 602 is cleavably linked to the first bead 601 via a cleavable linker 605. Furthermore, a particular sequence 606 is contained between the first barcode nucleic acid 602 and the cleavable linker 605. Furthermore, the first hybridize region 604 is a sequence complementary to the second hybridize region 615.

FIG. 6B(1) shows a hybridized complex. 610 represents a second bead linked to a second barcode nucleic acid. Here, the second barcode nucleic acid 612 is hybridized with a first hybridize region 604 of a first barcode nucleic acid 602 in a second hybridize region 615. Furthermore, as shown in FIG. 6B(2), by using a primer 607 having a sequence complementary to a particular sequence 606, DNAs complementary to the first barcode nucleic acid 602 and the second barcode nucleic acid 612 are synthesized, and further, a DNA complementary to the second barcode nucleic acid 612 is synthesized by template switching.

Figure 7:
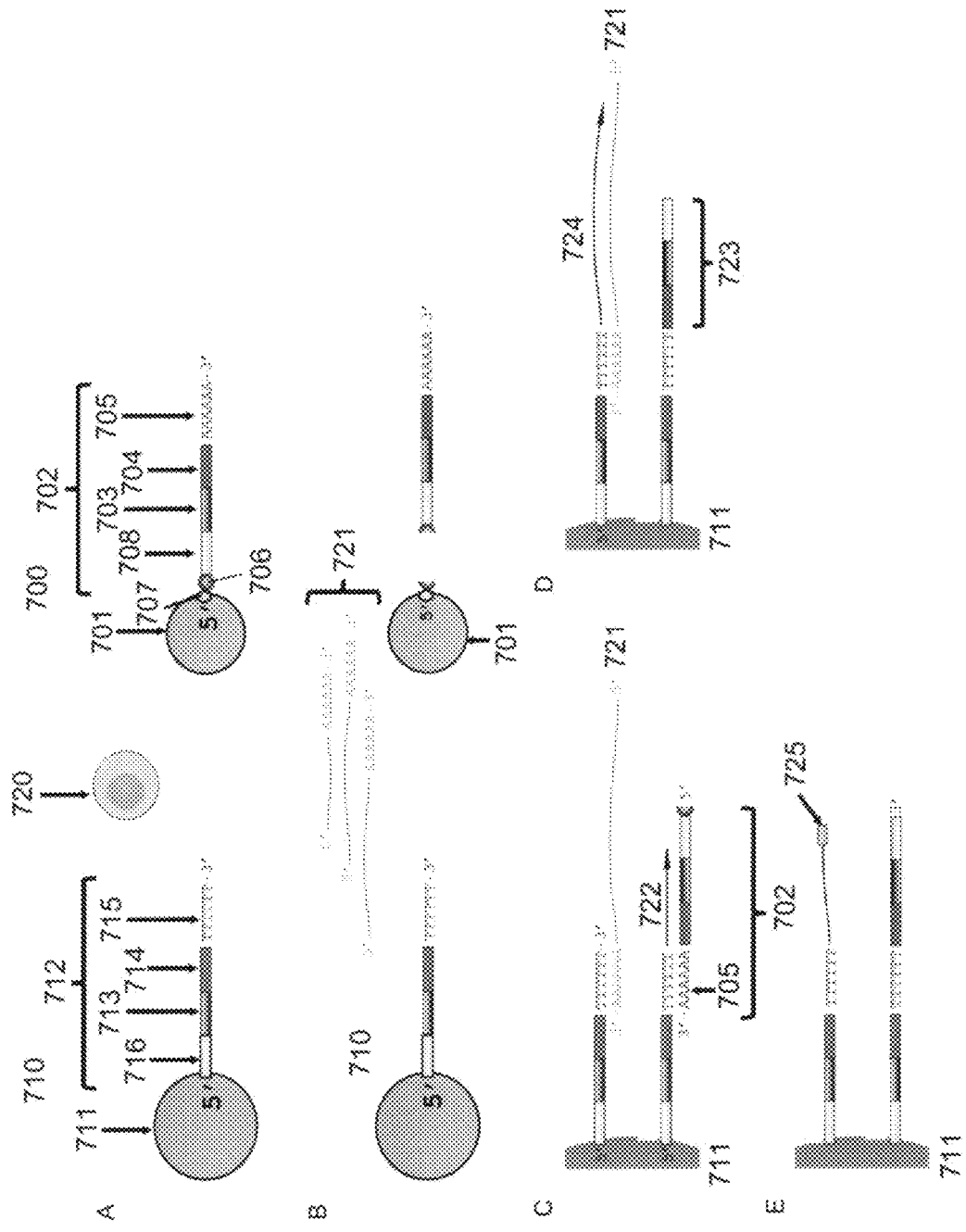
FIG. 7 is a schematic diagram showing another embodiment of the first bead(s) linked to the first barcode nucleic acid and the second bead(s) linked to the second barcode nucleic acid of the present invention.

Furthermore, another embodiment of the first bead(s) linked to the first barcode nucleic acid and the second bead(s) linked to the second barcode nucleic acid is shown in FIG. 7. FIG. 7 shows, as another embodiment, an embodiment in which each of the first barcode nucleic acid and the second barcode nucleic acid is a DNA.

FIG. 7A shows the step of preparing a compartment. In a first bead linked to a first barcode nucleic acid 700 in FIG. 7A, a first barcode nucleic acid 702 is linked to a first bead 701 having imaging information that can be clearly distinguished from each other. The first barcode nucleic acid 702 contains a first common barcode region 703 and a first hybridize region 705. The first barcode nucleic acid 702 contains a PCR primer region 708, the first common barcode region 703, a first unique barcode region 704, and the first hybridize region 705 in this order from the first bead side. Furthermore, the first barcode nucleic acid 702 is cleavably linked via a cleavable linker 706 to an acrylamide moiety 707 such as an acrylic phosphoramidite moiety (Acrydite (trademark)) bound to the first bead 701. Furthermore, the first hybridize region 705 is polyadenine.

In a second bead linked to a second barcode nucleic acid 710 in FIG. 7A, a second barcode nucleic acid 712 is linked to a second bead 711. The second barcode nucleic acid 712 contains a second common barcode region 713, a second unique barcode region 714, and a second hybridize region 715. The second barcode nucleic acid 712 contains a PCR primer region 716, the second common barcode region 713, the second unique barcode region 714, and the second hybridize region 715 in this order from the second bead side. The above second hybridize region 715 is polythymine. 720 represents a cell.

FIG. 7B to E shows the step of obtaining a hybridized complex after the step of associating nondestructive measurement information of a single cell with imaging information of a bead.

In FIG. 7B, a photocleavable linker is cleaved, and a cell is lysed. FIG. 7B shows a first bead 701 in which a first barcode nucleic acid 702 is cleaved, a second bead linked to a second barcode nucleic acid 710, and a cell-derived mRNA 721.

FIG. 7C shows a hybridized complex. Here, the second barcode nucleic acid 712 is hybridized with a first hybridize region 705 of a first barcode nucleic acid 702 in a second hybridize region 715. Furthermore, a complementary strand DNA 723 is synthesized by a DNA polymerase 722. Furthermore, the second barcode nucleic acid 712 is hybridized with polyadenine of the cell-derived mRNA 721 in a second hybridize region 715.

In FIG. 7D, in the hybridized complex, a reverse transcription is performed, and a cDNA 724 for the cell-derived mRNA 721 is synthesized.

In FIG. 7E, the 3' end of the synthesized cDNA is tagged with a DNA tag 725. The above DNA tag can be used as a PCR primer site, and examples thereof include a transposon Mosaic End (ME) sequence.

Method for Producing a Second Bead(s) Linked to a Plurality of Second Barcode Nucleic Acids A method for producing a second bead(s) linked to a plurality of second barcode nucleic acids can be performed by a known method. For example, production can be performed by the method mentioned in E. Z. Macosko et al., Highly Parallel Genome-wide Expression Profiling of Individual Cells Using Nanoliter Droplets. Cell. 161, 1202-1214 (2015).

When the above method is briefly described, the second common barcode region in the second barcode nucleic acid can be produced by split-and-pool synthesis. For example, it can be produced by performing n rounds of the split-and-pool synthesis. Each round is consisting of i) a step of splitting a bead population into four pieces, ii) a step of synthesizing any of A, G, C, and T for each bead population, and iii) a step of combining and pooling the four bead populations. The number of rounds n can be appropriately set according to the length of a barcode sequence to be produced. For example, n=6 to 40 is exemplified.

After the above second common barcode is produced, a second unique barcode region is synthesized. For all beads linked to the second common barcode region, synthesis in the presence of all bases of A, T, G, and C is performed for m rounds. The number of rounds m can be appropriately set according to the length of a barcode sequence to be produced. For example, m=3 to 15 is exemplified.

Partitioning

Figure 8A:
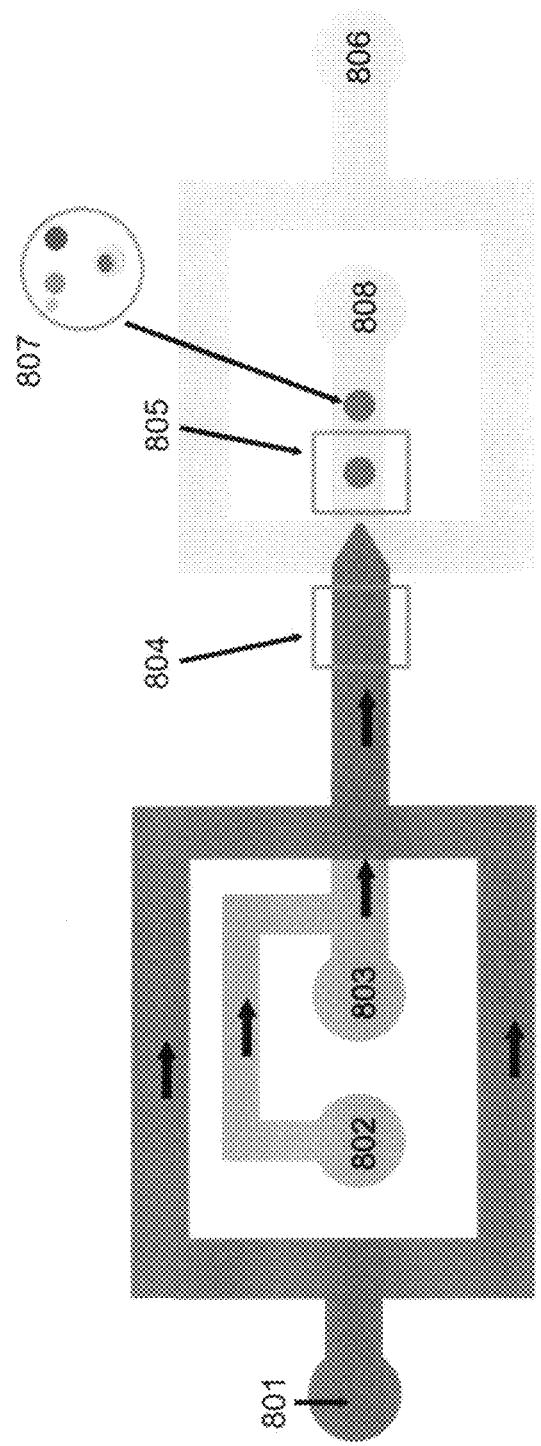
FIG. 8 is a schematic diagram showing a method for producing a compartment of the present invention.
Figure 8B:
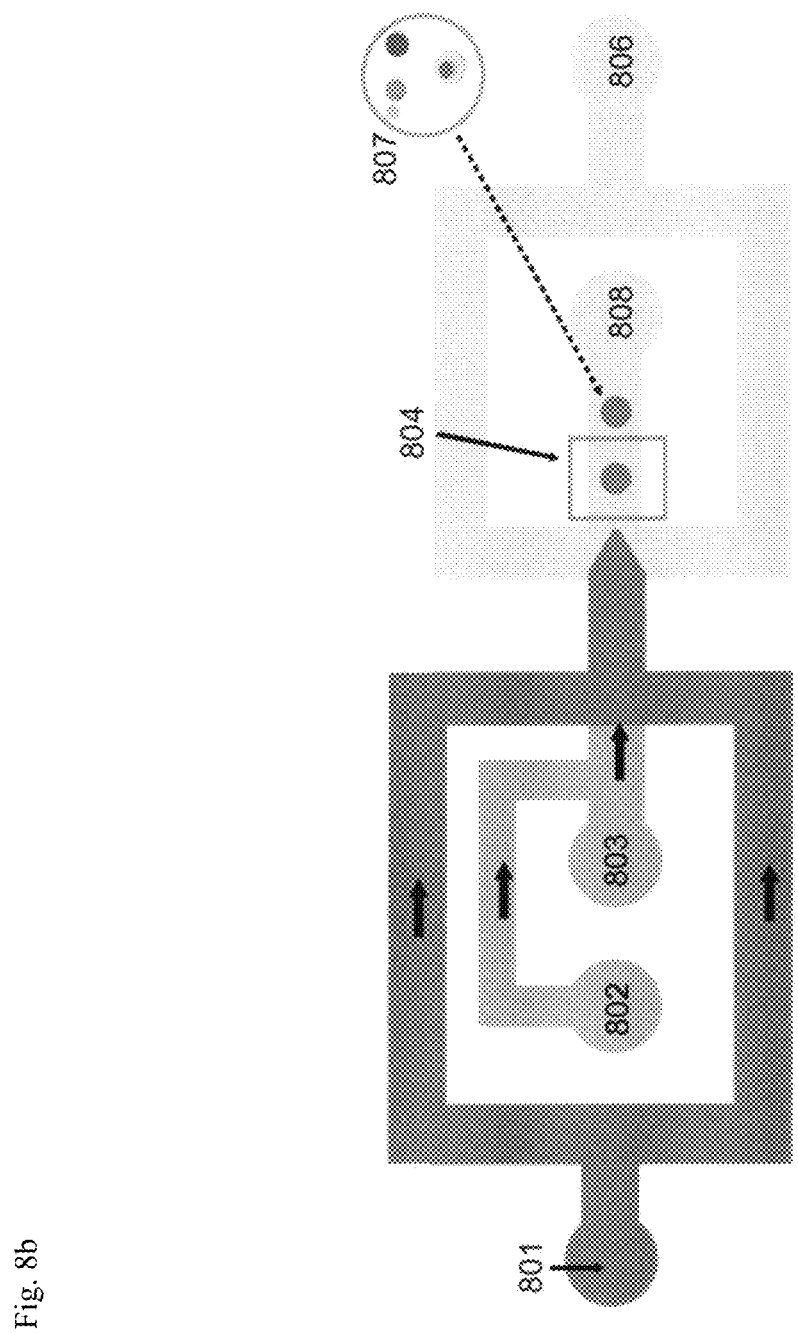
Figure 9:
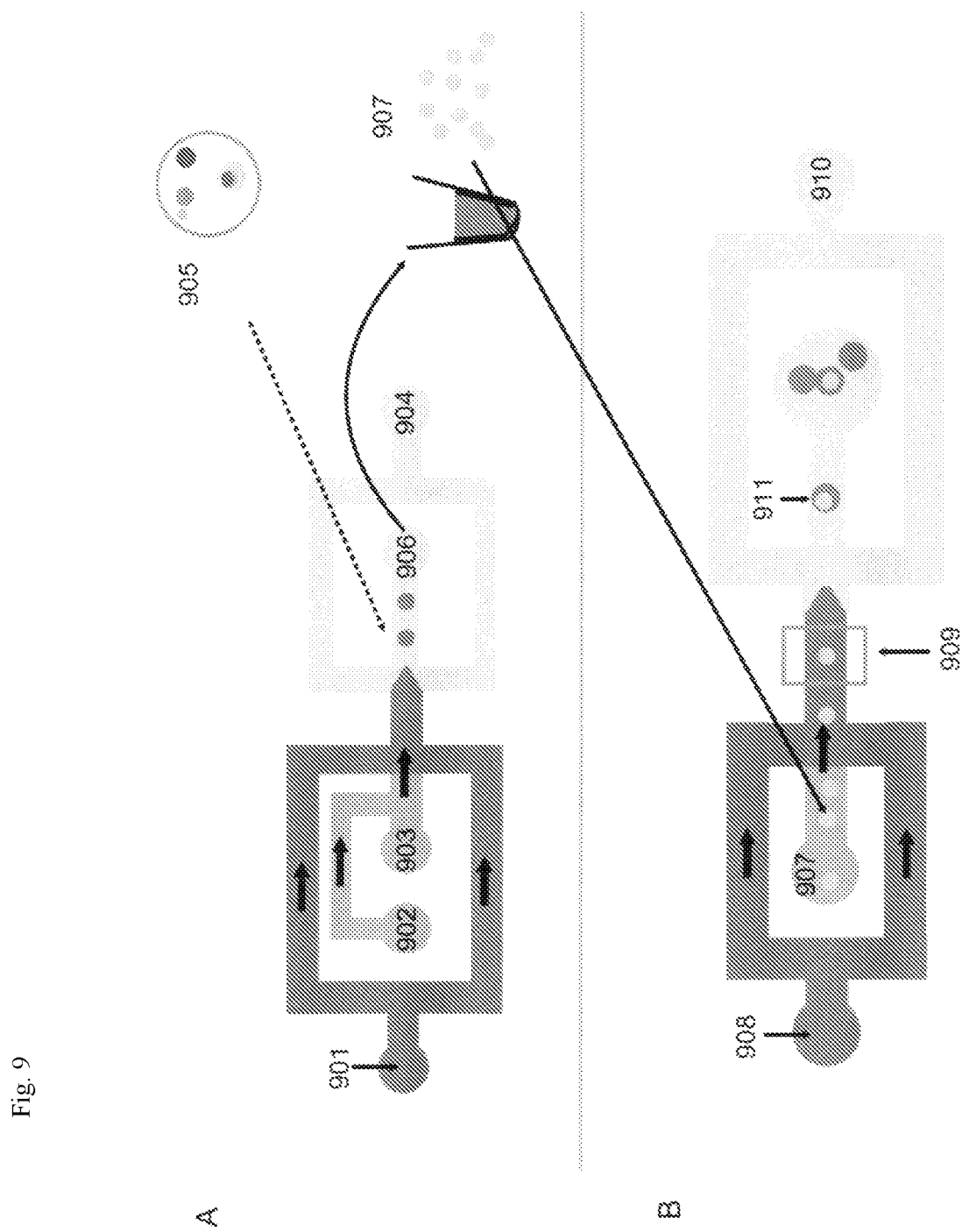
FIG. 9 is a schematic diagram showing another embodiment of the method for producing a compartment of the present invention.

Partitioning, namely, one embodiment of a method for producing a compartment is specifically described based on FIGS. 8 and 9.

FIGS. 8a and 8b shows a method for producing a compartment in a single step and detecting and/or measuring both nondestructive measurement information of single cells and imaging information of a first bead(s). Specifically, a solution containing a cell 801, a first bead(s) linked to a first barcode nucleic acid 802, and a second bead(s) linked to a second barcode nucleic acid 803 is put into an oil 806 to produce a droplet as a compartment 807, and the droplet is released through an outlet 808. Measurement of nondestructive measurement information is performed before and after formation of a compartment in FIG. 8a and performed after formation of a compartment in FIG. 8b. In FIG. 8a, it is possible to perform one type of measurement each before and after formation of a compartment, for example, fluorescence imaging measurement 804 and bright field imaging 805. Here, in the measurement before production of a compartment, correct imaging information of a cell and a first bead(s) can be obtained, and in the measurement after production of a compartment, a combination of a cell and a first bead(s) in the compartment can be confirmed. According to the methods in FIGS. 8a and 8b, it becomes possible to photograph a natural state of a cell and a first bead(s). In the above methods, examples of an apparatus specifically used include an apparatus used for a droplet production method using microfluidic techniques such as a flow focusing device for production of a compartment, and imaging flow cytometry, etc., for measurement of nondestructive measurement information. As the above apparatus, a known apparatus can be used as long as the present invention is not impaired. Examples of the apparatus used for a droplet production method using microfluidic techniques such as a flow focusing device include the apparatuses mentioned in E. Z. Macosko et al., Highly Parallel Genome-wide Expression Profiling of Individual Cells Using Nanoliter Droplets. Cell. 161, 1202-1214 (2015), Microfluid Nanofluid (2008) 5:585-594, Applied Physics Letters, Vol. 85, No. 13, 27, September 2004, p2649-2651, T. M. Gierahn et al., Seq-Well: portable, low-cost RNA sequencing of single cells at high throughput, Nature Methods, 14, 395-398 (2017), and JP 2013-508156 W and the like. According to the above apparatus used for a droplet production method using microfluidic techniques such as a flow focusing device, it is possible to efficiently produce a large amount of beads having imaging information including color, shape, and size.

FIG. 9 shows a method for producing a compartment in two steps. First, in step A, a solution containing a cell 901, a first bead(s) linked to a first barcode nucleic acid 902, and a second bead(s) linked to a second barcode nucleic acid 903 is put into an oil 904 to form a compartment 905, and then the compartment is released through an outlet 906 and gelated 907. Subsequently, step B shows a method in which the gelated particle 907 is released into an aqueous solvent containing a cell lysis buffer 908, fluorescence imaging measurement 909 is performed, and the particle is enclosed into an oil 910 to form a further compartment 911. According to the method of FIG. 9, although, when a cell in a compartment such as a droplet is photographed, the cell may rotate, a cell and a bead enclosed in a gel particle existing in an aqueous phase do not rotate, thus making stable photographing possible.

Figure 10:
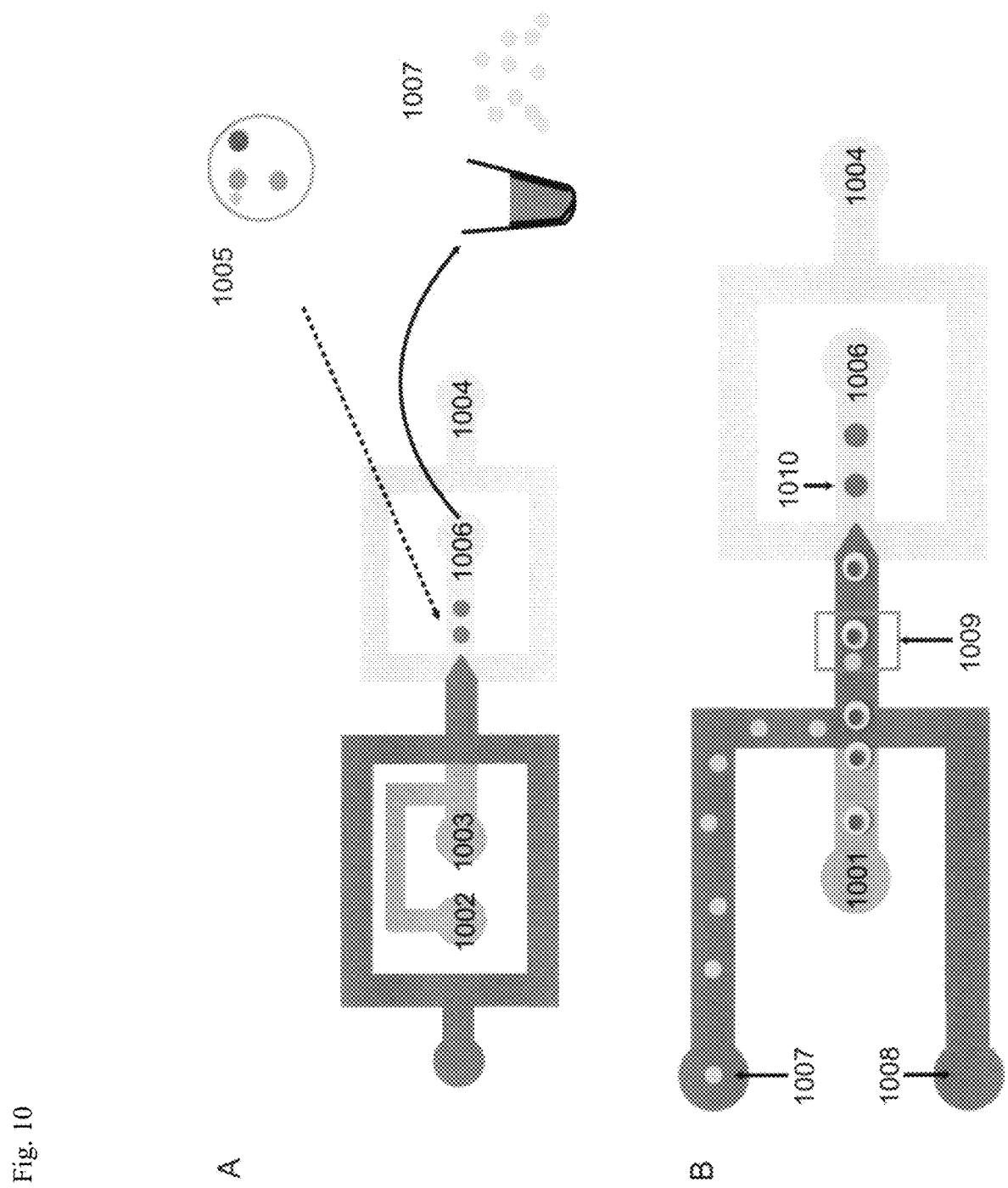
FIG. 10 is a schematic diagram showing another embodiment of the method for producing a compartment of the present invention.

FIG. 10 shows another embodiment of the method for producing a compartment in two steps. First, in step A, a solution containing a first bead(s) linked to a first barcode nucleic acid 1002 and a second bead(s) linked to a second barcode nucleic acid 1003 is put into an oil 1004 to form a compartment 1005, and then the compartment is released through an outlet 1006 and gelated 1007. Subsequently, step B shows a method in which the gelated particle 1007 and a cell 1001 are released into an aqueous solvent containing a cell lysis buffer 1008, fluorescence imaging measurement 1009 is performed, and the particle is enclosed into an oil 1004 to form a further compartment 1010. In the compartment enclosing the cell, the cell lysis buffer, the first bead(s), and the second bead(s), finally the lysis buffer lyses the cell and the gelated particle, thus making it possible to obtain a hybridized complex.

Figure 11:
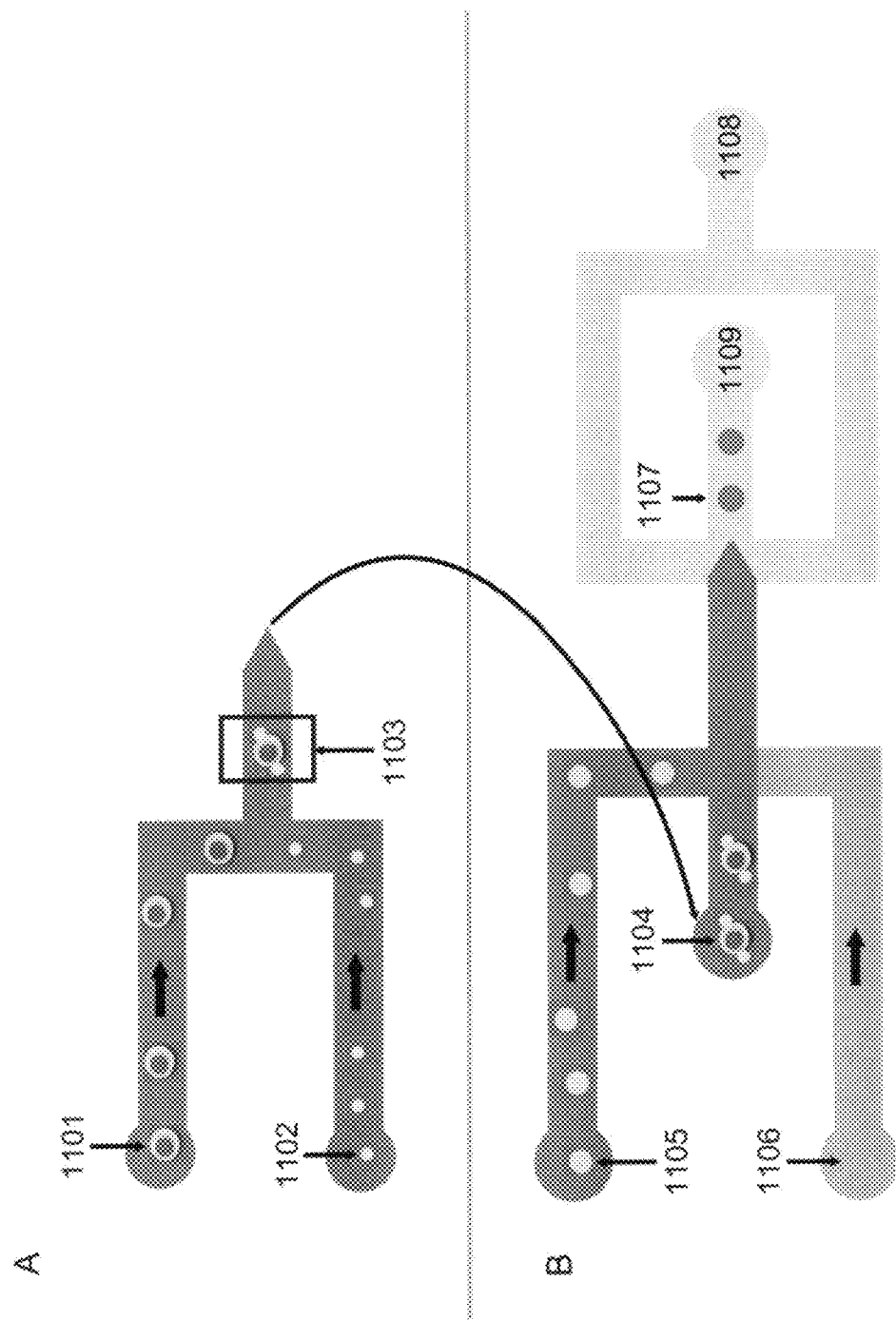
FIG. 11 is a schematic diagram showing another embodiment of the method for producing a compartment of the present invention.

FIG. 11 shows further another embodiment of the method for producing a compartment in two steps. First, in step A, a solution containing a first bead(s) linked to a first barcode nucleic acid 1102 and a cell 1101 is produced, followed by mixing. Then, for example, a cell carrying the first bead(s) is obtained in a flow pass. Fluorescence imaging measurement 1103 of the cell thus obtained is performed. Subsequently, in step B, a solution containing the cell carrying the first bead(s) 1104, a second bead(s) linked to a second barcode nucleic acid 1105, and an aqueous solvent containing a cell lysis buffer 1106 are mixed in a flow pass. The mixture thus obtained is released into a flow pass filled with an oil 1108, a droplet as a compartment 1107 is produced, and the droplet is released through an outlet 1109. The above method can also be utilized in an embodiment in which a derivative of a cell is contained in a compartment.

System

A system for integrally detecting nondestructive measurement information and genome-related information of single cells of the present invention is characterized by including a compartment-preparing portion which prepares a plurality of compartments containing a single cell or a derivative thereof, a first bead(s), and a second bead(s) per compartment, wherein each first bead is a particle cleavably linked to a first barcode nucleic acid corresponding to each imaging information or an organism containing a first barcode nucleic acid corresponding to each imaging information, and imaging information of the first bead(s) in each compartment can be clearly distinguished from each other, and the second bead(s) is linked to a plurality of second barcode nucleic acids hybridizable with a genome-related nucleic acid corresponding to a cell genome or an expressed product thereof or the first barcode nucleic acid; a nondestructive measurement information-measuring portion which measures both nondestructive measurement information of the single cell and imaging information of the first bead(s) and associates the nondestructive measurement information of the single cell with the imaging information of the first bead(s) before preparation of each compartment or in each compartment; a hybridized complex-forming portion which cleaves a first barcode nucleic acid corresponding to each imaging information from the associated first bead(s), and hybridizes each of the genome-related nucleic acid and the first barcode nucleic acid with the second barcode nucleic acid to obtain a hybridized complex; an amplified product-producing portion which produces an amplified product derived from the hybridized complex; and a nondestructive measurement information- and genome-related information-detecting portion which integrally detects nondestructive measurement information and genome-related information in the single cell using an expression pattern of the amplified product as an index.

This system will be described in accordance with the flow chart in FIG. 12.

In the compartment-preparing portion (A), a plurality of compartments containing single cells or a derivative thereof, a first bead(s), and a second bead(s) per compartment are prepared. The above plurality of compartments is preferably obtained by partitioning a cell group, a plurality of first beads, and a plurality of second beads. Here, each of the above first bead(s) is a particle cleavably linked to a first barcode nucleic acid corresponding to each imaging information or an organism containing a first barcode nucleic acid corresponding to each imaging information, and imaging information of the first bead(s) in each compartment can be clearly distinguished from each other. Furthermore, the above second bead is linked to a plurality of second barcode nucleic acids hybridizable with a genome-related nucleic acid corresponding to a cell genome or an expressed product thereof or the first barcode nucleic acid. Examples of the apparatus used as the above compartment-preparing portion include a device used for a droplet production method using microfluidic techniques such as a flow focusing device.

In the nondestructive measurement information- and imaging information-measuring portion (B), both nondestructive measurement information of single cells and imaging information of the first bead(s) are measured, and the nondestructive measurement information of single cells is associated with the imaging information of the first bead(s), before preparation of each compartment or in each compartment. Examples of the apparatus used for measurement of nondestructive measurement information include a flow cytometer or a microscope. When the compartment is in a form that is not destroyed by measurement of nondestructive measurement information or imaging information of a droplet or a gel particle or the like, nondestructive measurement information of a cell and imaging information of the first bead(s) can be measured again after one measurement. Re-measurement is advantageous in terms of the fact that change in nondestructive measurement information of a cell can be obtained sequentially.

When a derivative of a cell is contained in a compartment, it is preferable to measure and associate nondestructive measurement information of single cells and/with imaging information of the first bead(s) before preparation of the compartment. Therefore, before a compartment is prepared in the compartment-preparing portion (A), measurement and association of nondestructive measurement information of a single cell and/with imaging information of the first bead(s) may be performed in the nondestructive measurement information- and imaging information-measuring portion (B).

In the hybridized complex-forming portion (C), the unique first barcode nucleic acid is cleaved from the above associated first bead(s), and each of the above genome-related nucleic acid and the above first barcode nucleic acid is hybridized with the second barcode nucleic acid to obtain a hybridized complex. Examples of the apparatus and reagent used for formation of a hybridized complex include a device for cleaving a cleavable linker linked to the first barcode nucleic acid, and a reagent and a device for formation of a hybridized complex. The above device for cleaving a cleavable linker can be appropriately selected according to the type of the cleavable linker, and for example, when the cleavable linker is a UV-cleavable linker (e.g., iSpPC (Integrated DNA Technologies, Inc.)), a UV irradiation device (e.g., BlackRay xenon lamp-installed device) is exemplified. Examples of the reagent for formation of a hybridized complex include a usual reagent used for hybridization of a nucleic acid, and examples of the device include a water bath and the like.

In the amplified product-producing portion (D), an amplified product derived from the above hybridized complex is produced. As production of an amplified product, for example, when the genome-related nucleic acid is an RNA, reverse transcription and PCR are exemplified, and when the genome-related nucleic acid is a DNA, extension PCR is exemplified. Examples of the reagent used for production of the amplified product include a usual regent used for reverse transcription or PCR reaction, and examples of the apparatus include a PCR device.

In the nondestructive measurement information- and genome-related information-detecting portion (E), nondestructive measurement information and genome-related information of one cell are integrally detected using an expression pattern of the above amplified product as an index. The genome-related information is obtained by determining sequence information of the genome-related nucleic acid to a sequencer. The genome-related information thus obtained can be associated with nondestructive measurement information of a single cell by a computer.

The above embodiments of the system can be performed according to the description on the detection method of the present invention.

Combination

Another embodiment of the present invention is a combination of a first bead(s) and a second bead(s) for integrally detecting nondestructive measurement information and genome-related information of single cells, which is characterized by that the first bead(s) is a particle(s) cleavably linked to a first barcode nucleic acid corresponding to each imaging information or each first bead is an organism containing a first barcode nucleic acid corresponding to each imaging information, the second bead(s) is linked to a plurality of second barcode nucleic acids hybridizable with a genome-related nucleic acid corresponding to a cell genome or an expressed product thereof or the first barcode nucleic acid, nondestructive measurement information of a single cell can be detected using an expression pattern of a first amplified product derived from a hybridized complex of the first barcode nucleic acid with the second barcode nucleic acid as an index, and genome-related information of the single cell can be detected using an expression pattern of a second amplified product derived from a hybridized complex of the genome-related nucleic acid with the second barcode nucleic acid as an index. The combination of the present invention is not particularly limited as long as it is used for integrally detecting nondestructive measurement information and genome-related information of single cells, and the combination may be in a form of one composition or an agent such as a reagent, or may be composed of a combination of a plurality of compositions or agents such as reagents. The above combination may be composed integrally or as separate body. Examples of the above combination of a plurality of compositions or compositions as separate body include a combination of a composition including the first bead(s) and a composition including the second bead(s). Here, the above combination may be a reagent kit to be used for a method for integrally detecting nondestructive measurement information and genome-related information of single cells. The reagent kit may be provided with a buffer, a reagent necessary for reverse transcription or PCR reaction, a necessary reagent such as a cell lysis buffer, instructions for use or the like.

Detecting Agent Including a First Bead(s)

Another embodiment of the present invention is a detecting agent including a first bead(s), which is used together with a second bead(s) for integrally detecting nondestructive measurement information and genome-related information of single cells, which is characterized by that the first bead(s) is a particle(s) cleavably linked to a first barcode nucleic acid corresponding to each imaging information or each first bead is an organism containing a first barcode nucleic acid corresponding to each imaging information, the second bead(s) is linked to a plurality of second barcode nucleic acids hybridizable with a genome-related nucleic acid corresponding to a cell genome or an expressed product thereof or the first barcode nucleic acid, nondestructive measurement information of a single cell can be detected using an expression pattern of a first amplified product derived from a hybridized complex of the first barcode nucleic acid with the second barcode nucleic acid as an index, and genome-related information of the single cell can be detected using an expression pattern of a second amplified product derived from a hybridized complex of the genome-related nucleic acid with the second barcode nucleic acid as an index.

Detecting Agent Including a Second Bead(s)

A detecting agent including a second bead(s), which is used together with a first bead(s) for integrally detecting nondestructive measurement information and genome-related information of single cells, which is characterized by that the first bead(s) is a particle(s) cleavably linked to a first barcode nucleic acid corresponding to each imaging information or each first bead is an organism containing a first barcode nucleic acid corresponding to each imaging information, the second bead(s) is linked to a plurality of second barcode nucleic acids hybridizable with a genome-related nucleic acid corresponding to a cell genome or an expressed product thereof or the first barcode nucleic acid, nondestructive measurement information of a single cell can be detected using an expression pattern of a first amplified product derived from a hybridized complex of the first barcode nucleic acid with the second barcode nucleic acid as an index, and genome-related information of the single cell can be detected using an expression pattern of a second amplified product derived from a hybridized complex of the genome-related nucleic acid with the second barcode nucleic acid as an index.

Method for Obtaining Nondestructive Measurement Information and Genome-Related Information of Single Cells for a Test Substance As another embodiment of the present invention, it is possible to provide a method for obtaining nondestructive measurement information and genome-related information of single cells for a test substance, using the method for integrally detecting nondestructive measurement information and genome-related information of single cells of the present invention. The above method for obtaining nondestructive measurement information and genome-related information of single cells for a test substance is characterized by making the above test substance coexist with a single cell or a derivative thereof, the above first bead(s), and the above second bead(s) in a compartment. Examples of the timing of making the test substance coexist (e.g., timing of addition) include before, during, or after formation of a compartment. Examples of the test substance include a drug such as a low-molecular compound, a peptide, a protein, a nucleic acid, a virus or the like. The test substance in each compartment may be the same or different. The concentration of the test substance may be the same or different in each compartment.

Furthermore, it is possible to perform an assay such as screening of a test substance, using the nondestructive measurement information and the genome-related information of single cells for the test substance obtained by the above method. From the genome-related information and/or nondestructive measurement information of the cell thus obtained, response of the cell to the test substance (e.g., molecular expression/localization, form, change in differentiation, etc.) is measured, and based on the measurement results of the response, it is possible to perform an assay such as screening of the test substance.

Any of the above embodiments of the combination, the detecting agent including a first bead(s), the detecting agent including a second bead(s), and the obtaining method can be performed according to the description on the detection method of the present invention.

EXAMPLES

The present invention will be specifically described by way of Examples, but the present invention is not limited to these Examples. Unless otherwise specified, the measurement methods and the units of the present invention are in accordance with the provisions of the Japanese Industrial Standards (JIS).

Example 1: Production of a First Bead(s)

Production of a First Bead(s)

First, a fluorescently labeled sodium alginate solution was produced. Specifically, a fluorescent dye with a desired concentration was added to a 2% by mass sodium alginate solution to produce a green, red, or blue fluorescent sodium alginate solution. 5FTSC (fluorescein-5-thiosemicarbazide) was used as the green fluorescent dye, AF555 Hydrazide was used as the red fluorescent dye, and Cascade Blue Hydrazide was used as the blue fluorescent dye.

Next, a first barcode nucleic acid-linked sodium alginate solution was produced. Specifically, N-β-maleimidopropionic acid hydrazide (BMPH) was added to a sodium alginate solution to produce a BMPH-sodium alginate solution. To the BMPH-sodium alginate solution thus obtained, a first barcode nucleic acid in which the 5' end was thiol-modified was added, thus producing a first barcode nucleic acid-linked sodium alginate solution.

A dispersed phase solution obtained by mixing a 2% by mass sodium alginate mixture of the fluorescent sodium alginate solution and the first barcode nucleic acid-linked sodium alginate solution with a Ca-EDTA solution (50 mM-EDTA/50 mM sodium chloride, pH 7.2) in equal parts was obtained. Here, the first barcode nucleic acid having a first common barcode region which is common in the fluorescence of the same color was used. Next, according to the method mentioned in E. Z. Macosko et al., Highly Parallel Genome-wide Expression Profiling of Individual Cells Using Nanoliter Droplets. Cell. 161, 1202-1214 (2015), the dispersed phase solution was added to a continuous phase solution (a fluorine-based oil containing a surfactant), and a droplet was formed in the mixture thus obtained. Then, acetic acid was added to the mixture so that the concentration became 0.05% to release Ca from Ca-EDTA, and the droplet was gelated to produce a first barcode nucleic acid-linked fluorescent alginic acid bead (hereinafter also referred to as first bead(s), or green, red, or blue fluorescent first bead(s)). The first bead(s) in the mixture was isolated by washing with 1H,1H,2H,2H-perfluorooctanol.

Confirmation of Fluorescence Stability of the Bead

To 5 mL of a TEBST buffer (10 mM Tris-HCl [pH 8.0], 137 mM NaCl, 2.7 mM KCl, and 0.1% (v/v) Triton X-100), about 10,000,000 first beads (green, red, or blue fluorescent first beads) were added to suspend. At time points of 0 hour and 72 hours after addition of the buffer, the brightness of the first beads was confirmed by flow cytometry. As a result, no change in the fluorescence spectrum was observed at time points of 0 hour and 72 hours.

Example 2: Production of a Compartment (a Water-in-Oil Droplet Containing a First Bead(s), a Second Bead, and a Cell)

According to the method mentioned in E. Z. Macosko et al., Highly Parallel Genome-wide Expression Profiling of Individual Cells Using Nanoliter Droplets. Cell. 161, 1202-1214 (2015), a water-in-oil compartment containing the first bead(s) obtained in Example 1, a second bead (Chemgenes Corporation), and a NIH3T3 cell was produced by a droplet production method using microfluidic techniques. Here, the second barcode nucleic acid in the second bead was linked to the second bead via a linker. The second barcode nucleic acid was polythymine of 7 bases, a PCR primer region of 25 bases, a second common barcode region of 12 bases, a second unique barcode region of 8 bases, and polythymine (a second hybridize region) of 30 bases in this order from the second bead side. A photograph of the compartment thus obtained is shown in FIG. 13.

Example 3: Preparation of a First Bead-Carrying Cell (a) Green Fluorescent First Bead-Carrying NIH3T3 Cell $5 \times 10^5$ NIH3T3 cells that were removed from the culture plate and fixed with CellCover and $5 \times 10^5$ green fluorescent first beads obtained in Example 1 were incubated at 4° C. for 40 hours, followed by further centrifugation at 4° C. and 150 G for 1 hour to promote adhesion, thus obtaining a green fluorescent first bead-carrying NIH3T3 cell. Alginic acid constituting the green fluorescent first bead(s) contained 50% of alginic acid modified with a BAM reagent (a cell membrane modifier). A composite photograph of the obtained cell taken by a fluorescence microscope and a bright field microscope is shown in FIG. 14A.

(b) Red Fluorescent First Bead-Carrying K562 Cell

By the same method as in (a) except that the cell was a K562 cell and the first bead(s) was the red fluorescent first bead(s), a red fluorescent first bead-carrying K562 cell was obtained. A composite photograph of the obtained cell taken by a fluorescence microscope and a bright field microscope is shown in FIG. 14B.

(c) Green Fluorescent First Bead- and Red Fluorescent First Bead-Carrying MIA-PaCa2 Cell By the same method as in (a) except that the cell was a MIA-PaCa2 cell, the first bead(s) was the green fluorescent first bead(s) and the red fluorescent first bead(s), a green fluorescent first bead- and red fluorescent first bead-carrying MIA-PaCa2 cell was obtained. A composite photograph of the obtained cell taken by a fluorescence microscope and a bright field microscope is shown in FIG. 14C.

Example 4: Verification That Imaging Information from the First Bead(s) and the First Common Barcode Region Corresponding Thereto are Obtained Production of a Compartment (a Compartment Containing a First Bead(s) Containing a Cell, and a Second Bead)

By the same method as in Example 1 except that a cell (an NIH3T3 cell, a K562 cell, or a MIA-PaCa2 cell) was added to the dispersed phase solution, a green, red, or blue fluorescent first bead(s) was produced. Therefore, the above first bead(s) contained a cell. Each first bead of the same color contained the same type of a cell. The results are shown in FIG. 15. FIG. 15A shows the result of observation with a phase-contrast microscope, and FIG. 15B shows a composite photograph taken by a fluorescence microscope and a bright field microscope.

Next, according to the method mentioned in E. Z. Macosko et al., Highly Parallel Genome-wide Expression Profiling of Individual Cells Using Nanoliter Droplets. Cell. 161, 1202-1214 (2015), a compartment containing the above cell-containing first bead(s) and the second bead mentioned in Example 2 (Chemgenes Corporation) was produced by a droplet production method using microfluidic techniques. The same compartment except that no first bead is contained was also produced. Here, the compartment containing no first bead contains a cell, as with the above compartment containing the first bead(s).

Base sequence analysis of whole sequencing of an amplified product derived from a hybridized complex in the compartment obtained above was performed. Of the analysis results, the number of reads having 15 bases including a sequence of the first common barcode region was counted. The results are shown in Table 1.

TABLE 1

| | Number of reads of the first common barcode region | | |
|---|---|---|---|
| | Green fluorescent first bead | Red fluorescent first bead | Blue fluorescent first bead |
| Compartment containing the first bead(s) (total of 26,400,000 reads) | 8430 | 27879 | 24838 |
| Compartment containing no first bead (total of 28,700,000 reads) | 12 | 0 | 1 |

As shown in the above results, it was possible to read the first common barcode region corresponding to imaging information of the first bead(s).

Example 5: Verification that Imaging Information of the First Bead(s) Can Be Associated with Genome-Related Information of a Cell According to the method mentioned in E. Z. Macosko et al., Highly Parallel Genome-wide Expression Profiling of Individual Cells Using Nanoliter Droplets. Cell. 161, 1202-1214 (2015) or T. M. Gierahn et al., Seq-Well: portable, low-cost RNA sequencing of single cells at high throughput, Nature Methods, 14, 395-398 (2017), a compartment containing a cell carrying the first bead(s) obtained in Example 3 and the second bead mentioned in Example 2 was produced by a droplet production method using microfluidic techniques. Here, as the first bead-carrying cell, a mixture of a green fluorescent first bead-carrying NIH3T3 cell (a mouse-derived cell) and a red fluorescent first bead-carrying K562 cell (a human-derived cell) was used. In preparation of the compartment, adjustment was performed so that any one of the green fluorescent first bead-carrying NIH3T3 cell and the red fluorescent first bead-carrying K562 cell was contained in each compartment.

Then, base sequence analysis of an amplified product derived from a hybridized complex in the compartment thus obtained was performed. Specifically, in the compartment to which the red fluorescent first bead(s) belonged, ranking was performed based on the number of reads that are matched to 10 bases of the first common barcode region of the red fluorescent first bead(s) (here, a plurality of first barcode nucleic acids are linked to the bead(s)), and 100 reads in the descending order were selected. Furthermore, the number of gene transcription products in the compartment to which these reads belong was measured. The results are shown in FIG. 16. The plots in the figure represent the number of mouse gene transcription products for the vertical axis and the number of human gene transcription products for the horizontal axis. From FIG. 16, it was revealed that imaging information of the first bead(s) is associated with genome-related information of a cell.

Example 6: Organism Containing a First Barcode Nucleic Acid Corresponding to Imaging Information A bacterium containing a plasmid having a fluorescent protein gene region and a first common barcode region was produced. Specifically, a bacterium containing a plasmid having an EGFP protein gene region and a first common barcode region corresponding to EGFP, a plasmid having a Venus protein gene region and a first common barcode region corresponding to Venus, or a plasmid having an EBFP protein gene region and a first common barcode region corresponding to EBFP was produced. A composite photograph of a mixture of the obtained bacteria taken by a fluorescence microscope and a bright field microscope is shown in FIG. 17A.

FIG. 17B shows the result of sequencing of the sequence of the plasmid having an EGFP protein gene region and a first common barcode region corresponding to EGFP. Subsequent to the EGFP protein gene region, a sequence region unique to each colony of the bacterium (a third unique barcode region), the first common barcode region corresponding to EGFP, and a polyA sequence region were confirmed.

According to the method mentioned in E. Z. Macosko et al., Highly Parallel Genome-wide Expression Profiling of Individual Cells Using Nanoliter Droplets. Cell. 161, 1202-1214 (2015), a water-in-oil compartment containing a bacterium containing the first barcode nucleic acid and a cell was produced by a droplet production method using microfluidic techniques. A photograph of the compartment thus obtained is shown in FIG. 17C. Then, the size of an amplified product derived from a hybridized complex in the compartment thus obtained was measured. As a result, it was possible to detect 288 bases containing the sequence of the third unique barcode region and the first common barcode region corresponding to EGFP. The results are shown in FIG. 17D.

REFERENCE SIGNS LIST

101 Cell group
102 First bead
103 Second bead
104 Compartment
105 Single cell
106 First barcode nucleic acid
107 Cell-derived mRNA
108 Second barcode nucleic acid
109 cDNA for first barcode nucleic acid
110 cDNA for cell-derived mRNA
111 Amplified product
112 First amplified product
113 Second amplified product
114 Nondestructive measurement information of cell
115 Transcriptome information of cell
116 Clustering
117 Cell type
120 Hybridized complex
201 First bead
202 First barcode nucleic acid
203 First common barcode region
204 First hybridize region
205 Cleavable linker
301 Second bead
302 Second barcode nucleic acid
303 Second common barcode region
304 Second unique barcode region
305 Second hybridize region
306 PCR primer region
400 First bead linked to first barcode nucleic acid
401 First bead
402 First barcode nucleic acid
403 First common barcode region
404 First hybridize region
405 Cleavable linker
410 Second bead linked to second barcode nucleic acid
411 Second bead
412 Second barcode nucleic acid
413 Second common barcode region
414 Second unique barcode region
415 Second hybridize region
416 PCR primer region
420 Cell
421 Particular sequence of genome-related nucleic acid
422 Genome-related nucleic acid
430 Compartment
500 First bead linked to first barcode nucleic acid
501 First bead
502 First barcode nucleic acid
503 First common barcode region
504 First hybridize region
505 Cleavable linker
510 Second bead linked to second barcode nucleic acid
511 Second bead
512 Second barcode nucleic acid
513 Second common barcode region
514 Second unique barcode region
515 Second hybridize region
516 PCR primer region
520 Nucleic acid probe
521 Molecule binding specifically to a molecule such as target protein expressed in single cell
522 Third barcode nucleic acid
523 Third common barcode region
524 Third hybridize region
525 Cleavable linker
530 Cell
540 Compartment
600 First bead linked to first barcode nucleic acid
601 First bead
602 First barcode nucleic acid
603 First common barcode region
604 First hybridize region
605 Cleavable linker
606 Particular sequence
607 Primer having sequence complementary to particular sequence
610 Second bead linked to second barcode nucleic acid
612 Second barcode nucleic acid
615 Second hybridize region
700 First bead linked to first barcode nucleic acid
701 First bead
702 First barcode nucleic acid
703 First common barcode region
704 First unique barcode region
705 First hybridize region
706 Cleavable linker
707 Acrylamide moiety
708 PCR primer region
710 Second bead linked to second barcode nucleic acid
711 Second bead
712 Second barcode nucleic acid
713 Second common barcode region
714 Second unique barcode region
715 Second hybridize region
716 PCR primer region
720 Cell
721 Cell-derived mRNA
722 DNA polymerase
723 Complementary strand DNA
724 cDNA for cell-derived mRNA
801 Cell
802 First bead(s) linked to first barcode nucleic acid
803 Second bead linked to second barcode nucleic acid
804 Fluorescence imaging measurement
805 Bright field imaging
806 Oil
807 Compartment
808 Outlet
901 Cell
902 First bead(s) linked to first barcode nucleic acid
903 Second bead linked to second barcode nucleic acid
904 Oil
905 Compartment
906 Outlet
907 Gelated particle
908 Cell lysis buffer
909 Fluorescence imaging measurement
910 Oil
911 Compartment
1001 Cell
1002 First bead(s) linked to first barcode nucleic acid
1003 Second bead linked to second barcode nucleic acid
1004 Oil
1005 Compartment
1006 Outlet
1007 Gelated particle 1008 Cell lysis buffer
1009 Fluorescence imaging measurement
1010 Compartment
1101 Cell
1102 First bead(s) linked to first barcode nucleic acid
1103 Fluorescence imaging measurement
1104 First bead-carrying cell
1105 Second bead linked to second barcode nucleic acid
1106 Cell lysis buffer
1107 Compartment
1108 Oil
1109 Outlet

The invention claimed is:

1. A method for integrally detecting nondestructive measurement information and genome-related information of single cells, the method comprising:
preparing a plurality of compartments containing a single cell or a derivative thereof, a first bead(s), and a second bead(s) per one compartment,
wherein each first bead is
a particle cleavably linked to a first barcode nucleic acid corresponding to imaging data of the first bead
or
an organism containing a first barcode nucleic acid corresponding to imaging data of the first bead, wherein the organism is configured to be lysed to release the first barcode nucleic acid, and
the imaging data of the first beads in the plurality of compartments can be clearly distinguished from each other, and
the second bead(s) is linked to a plurality of second barcode nucleic acids hybridizable with a genome-related nucleic acid corresponding to a cell genome or an expressed product thereof and the first barcode nucleic acid;
detecting both nondestructive measurement information of the single cell and the imaging data of the first bead(s) and associating the nondestructive measurement information of the single cell with the imaging data of the first bead(s) before preparation of each compartment or in each compartment;
cleaving the first barcode nucleic acid from the associated first bead(s), and hybridizing each of the genome-related nucleic acid and the first barcode nucleic acid with the second barcode nucleic acid to obtain a hybridized complex;
producing an amplified product derived from the hybridized complex; and
integrally detecting the nondestructive measurement information and genome-related information in the single cell using an expression pattern of the amplified product as an index.

2. The method according to claim 1, wherein
the nondestructive measurement information of the single cell is detected using an expression pattern of a first amplified product derived from a hybridized complex of the first barcode nucleic acid with the second barcode nucleic acid as an index, and
the genome-related information of the single cell is detected using an expression pattern of a second amplified product derived from a hybridized complex of the genome-related nucleic acid with the second barcode nucleic acid as an index.

3. The method according to claim 1, which is characterized by at least any one of (a) to (c):
(a) the number of the first beads per the one compartment is plural,
(b) the number of the second beads per the one compartment is one,
(c) the compartment is in a form of a well, a droplet, or a gel particle.

4. The method according to claim 1, wherein the genome-related nucleic acid is a genome DNA of the single cell, an RNA derived from a genome of the single cell or a cDNA thereof, or a nucleic acid probe specific to a protein expressed in the single cell.

5. The method according to claim 1, wherein the nondestructive measurement information is based on at least one piece of measurement information selected from color, fluorescence, size, shape, electromagnetic wave, transmission, phase, scattering, reflection, coherent Raman, Raman, and absorption spectrum.

6. The method according to claim 1, wherein each first barcode nucleic acid in the first bead(s) contains a first common barcode region which is common in the first bead(s) corresponding to the same imaging data and a first hybridize region hybridizable with the second barcode nucleic acid.

7. The method according to claim 6, wherein sequence information of the first common barcode region can be used as an index for identifying the nondestructive measurement information of the single cell.

8. The method according to claim 1, wherein each of the plurality of second barcode nucleic acids linked to the second bead(s) comprises a second common barcode region which is in common with each other, a second unique barcode region which can be clearly distinguished from each other, and a second hybridize region hybridizable with the genome-related nucleic acid or the first barcode nucleic acid.

9. The method according to claim 8, wherein sequence information of the second common barcode region can be used as an index for identifying the single cell or a derivative thereof existing in the compartment.

10. The method according to claim 8, wherein sequence information of the second unique barcode region can be used as an index for identifying the genome-related nucleic acid.

11. The method according to claim 1, wherein the second barcode nucleic acid further comprises a PCR primer region.

12. The method according to claim 8, wherein each first barcode nucleic acid in the first bead(s) contains a first common barcode region which is common in the first bead(s) corresponding to the same image and a first hybridize region hybridizable with the second barcode nucleic acid, and wherein the second hybridize region comprises the first hybridize region or a nucleic acid complementary to the genome-related nucleic acid.

13. A system for integrally detecting nondestructive measurement information and genome-related information of single cells, the system comprising:
a compartment-preparing portion which prepares a plurality of compartments containing a single cell or a derivative thereof, a first bead(s), and a second bead(s) per one compartment,
wherein each first bead is
a particle cleavably linked to a first barcode nucleic acid corresponding to imaging data of the first bead
or
an organism containing a first barcode nucleic acid corresponding to imaging data of the first bead, wherein the organism is configured to be lysed to release the first barcode nucleic acid, and
the imaging data of the first beads in the plurality of compartments can be clearly distinguished from each other, and the second bead(s) is linked to a plurality of second barcode nucleic acids hybridizable with a genome-related nucleic acid corresponding to a cell genome or an expressed product thereof and the first barcode nucleic acid;

a measurement instrument which measures both nondestructive measurement information of the single cell and the imaging data of the first bead(s) and associates the nondestructive measurement information of the single cell with the imaging data of the first bead(s) before preparation of each compartment or in each compartment;

a hybridizer which cleaves a first barcode nucleic acid corresponding to each imaging data from the associated first bead(s), and hybridizes each of the genome-related nucleic acid and the first barcode nucleic acid with the second barcode nucleic acid to obtain a hybridized complex;

an amplifier which produces an amplified product derived from the hybridized complex; and a detector which integrally detects the nondestructive measurement information and genome-related information in the single cell using an expression pattern of the amplified product as an index.

14. The system according to claim 13, wherein the measurement instrument comprises at least one selected from a microscope and a flow cytometer.

15. A combination of a first bead(s) and a second bead(s) for integrally detecting nondestructive measurement information and genome-related information of single cells, wherein the first bead(s) is
a particle(s) cleavably linked to a first barcode nucleic acid corresponding to imaging data of the first bead or
an organism(s) containing a first barcode nucleic acid corresponding to imaging data of the first bead, wherein the organism is configured to be lysed to release the first barcode nucleic acid, the second bead(s) is linked to a plurality of second barcode nucleic acids hybridizable with a genome-related nucleic acid corresponding to a cell genome or an expressed product thereof and the first barcode nucleic acid, the nondestructive measurement information of a single cell can be detected using an expression pattern of a first amplified product derived from a hybridized complex of the first barcode nucleic acid with the second barcode nucleic acid as an index, and the genome-related information of the single cell can be detected using an expression pattern of a second amplified product derived from a hybridized complex of the genome-related nucleic acid with the second barcode nucleic acid as an index.

16. A detecting agent comprising a first bead(s), which is used together with a second bead(s) for integrally detecting nondestructive measurement information and genome-related information of single cells, wherein the first bead(s) is
a particle(s) cleavably linked to a first barcode nucleic acid corresponding to imaging data of the first bead or
an organism(s) containing a first barcode nucleic acid corresponding to imaging data of the first bead, wherein the organism is configured to be lysed to release the first barcode nucleic acid, the second bead(s) is linked to a plurality of second barcode nucleic acids hybridizable with a genome-related nucleic acid corresponding to a cell genome or an expressed product thereof and the first barcode nucleic acid, nondestructive measurement information of a single cell can be detected using an expression pattern of a first amplified product derived from a hybridized complex of the first barcode nucleic acid with the second barcode nucleic acid as an index, and genome-related information of the single cell can be detected using an expression pattern of a second amplified product derived from a hybridized complex of the genome-related nucleic acid with the second barcode nucleic acid as an index.

17. A detecting agent comprising a second bead(s), which is used together with a first bead(s) for integrally detecting nondestructive measurement information and genome-related information of single cells, wherein the first bead(s) is
a particle(s) cleavably linked to a first barcode nucleic acid corresponding to imaging data of the first bead or
an organism(s) containing a first barcode nucleic acid corresponding to imaging data of the first bead, wherein the organism is configured to be lysed to release the first barcode nucleic acid, the second bead(s) is linked to a plurality of second barcode nucleic acids hybridizable with a genome-related nucleic acid corresponding to a cell genome or an expressed product thereof and the first barcode nucleic acid, nondestructive measurement information of a single cell can be detected using an expression pattern of a first amplified product derived from a hybridized complex of the first barcode nucleic acid with the second barcode nucleic acid as an index, and genome-related information of a single cell can be detected using an expression pattern of a second amplified product derived from a hybridized complex of the genome-related nucleic acid with the second barcode nucleic acid as an index.

18. A method for classifying a test cell, based on nondestructive measurement information in the test cell, using a classification model obtained based on the nondestructive measurement information and the genome-related information integrally detected by the method according to claim 1.

19. A method for obtaining nondestructive measurement information and genome-related information of single cells for a test substance, using the method for integrally detecting nondestructive measurement information and genome-related information of the single cells according to claim 1, the method comprising:

including coexistence with the single cell or the derivative thereof, the first bead(s), and the second bead(s).

20. A method for screening a test substance, using the nondestructive measurement information and the genome-related information of the single cell for the test substance obtained by the method according to claim 19.

21. The method according to claim 1, the imaging data are selected from color, fluorescence, size, shape, electromagnetic wave, transmission, phase, scattering, reflection, coherent Raman, infrared spectroscopy, Raman spectroscopy, absorption spectrum, and the number of first beads.

* * * * *